(12) United States Patent
Whisler et al.

(10) Patent No.: US 11,452,806 B2
(45) Date of Patent: Sep. 27, 2022

(54) OUTFLOW COLLECTION VESSELS, SYSTEMS, AND COMPONENTS THEREOF FOR HYSTEROSCOPIC SURGICAL PROCEDURES

(71) Applicant: COVIDIEN LP, Mansfield, MA (US)

(72) Inventors: Jordan A. Whisler, Brookline, MA (US); Timothy J. Wood, Wilmington, MA (US); Chad A. Pickering, Woburn, MA (US); Nikolai D. Begg, Wellesley, MA (US); Dalia Leibowitz, Cambridge, MA (US); Allen X. An, Woburn, MA (US)

(73) Assignee: Covidien LP, Mansfield, MA (US)

( * ) Notice: Subject to any disclaimer, the term of this patent is extended or adjusted under 35 U.S.C. 154(b) by 144 days.

(21) Appl. No.: 16/593,605

(22) Filed: Oct. 4, 2019

(65) Prior Publication Data

US 2021/0100936 A1    Apr. 8, 2021

(51) Int. Cl.
*A61M 1/00* (2006.01)
*A61B 17/32* (2006.01)
*A61B 17/00* (2006.01)
*A61B 17/42* (2006.01)

(52) U.S. Cl.
CPC ..... *A61M 1/602* (2021.05); *A61B 17/320016* (2013.01); *A61M 1/70* (2021.05); *A61B 2017/00199* (2013.01); *A61B 2017/4216* (2013.01); *A61B 2217/005* (2013.01); *A61M 2209/084* (2013.01)

(58) Field of Classification Search
CPC .......... A61M 1/0015; A61M 2209/084; A61M 1/602; A61M 1/70; A61M 1/604; A61M 1/62; A61M 1/68; A61M 1/682; A61M 1/684; A61B 17/320016; A61B 2217/005; A61B 2017/00199; A61B 2017/4216
See application file for complete search history.

(56) References Cited

U.S. PATENT DOCUMENTS

| 1,585,934 | A | 5/1926 | Muir |
| 1,666,332 | A | 4/1928 | Hirsch |
| 1,831,786 | A | 11/1931 | Duncan |

(Continued)

FOREIGN PATENT DOCUMENTS

| DE | 3206381 A1 | 9/1983 |
| DE | 3339322 A1 | 5/1984 |

(Continued)

*Primary Examiner* — Adam Marcetich
(74) *Attorney, Agent, or Firm* — Carter, DeLuca & Farrell LLP

(57) ABSTRACT

A collection system for collecting outflow from a hysteroscopic surgical procedure includes a collection vessel and a mounting stand. The collection vessel defines an internal volume and includes a top portion and a bottom portion. The collection vessel is transitionable between a collapsed configuration and an expanded configuration. The mounting stand includes an upper retainer and a lower retainer. The upper retainer of the mounting stand is configured to retain the top portion of the collection vessel and the lower retainer of the mounting stand is configured to retain the bottom portion of the collection vessel. The upper and lower retainers are configured to retain the collection vessel thereon in the expanded configuration.

19 Claims, 11 Drawing Sheets

(56) References Cited

U.S. PATENT DOCUMENTS

| | | | |
|---|---|---|---|
| 2,397,257 A * | 3/1946 | Goland | A61M 1/0011 |
| | | | D24/111 |
| 2,708,437 A | 5/1955 | Hutchins | |
| 3,297,022 A | 1/1967 | Wallace | |
| 3,686,706 A | 8/1972 | Finley | |
| 3,734,099 A | 5/1973 | Bender et al. | |
| 3,752,158 A * | 8/1973 | Kariher | A61M 1/0011 |
| | | | 604/133 |
| 3,791,379 A | 2/1974 | Storz | |
| 3,809,087 A * | 5/1974 | Lewis, Jr. | A61M 1/0011 |
| | | | 604/134 |
| 3,812,855 A | 5/1974 | Banko | |
| 3,835,842 A | 9/1974 | Iglesias | |
| 3,850,162 A | 11/1974 | Iglesias | |
| 3,945,375 A | 3/1976 | Banko | |
| 3,980,252 A | 9/1976 | Tae | |
| 3,995,619 A | 12/1976 | Glatzer | |
| 3,996,921 A | 12/1976 | Neuwirth | |
| 4,011,869 A | 3/1977 | Seiler, Jr. | |
| 4,108,182 A | 8/1978 | Hartman et al. | |
| 4,136,696 A * | 1/1979 | Nehring | A61M 3/0212 |
| | | | 604/142 |
| 4,146,405 A | 3/1979 | Timmer et al. | |
| 4,198,958 A | 4/1980 | Utsugi | |
| 4,203,444 A | 5/1980 | Bonnell et al. | |
| 4,210,146 A | 7/1980 | Banko | |
| 4,246,902 A | 1/1981 | Martinez | |
| 4,247,180 A | 1/1981 | Norris | |
| 4,258,721 A | 3/1981 | Parent et al. | |
| 4,261,346 A | 4/1981 | Wettermann | |
| 4,294,234 A | 10/1981 | Matsuo | |
| 4,316,465 A | 2/1982 | Dotson, Jr. | |
| 4,369,768 A | 1/1983 | Vukovic | |
| 4,392,485 A | 7/1983 | Hiltebrandt | |
| 4,414,962 A | 11/1983 | Carson | |
| 4,449,538 A | 5/1984 | Corbitt et al. | |
| 4,493,698 A | 1/1985 | Wang et al. | |
| 4,517,977 A | 5/1985 | Frost | |
| 4,543,965 A | 10/1985 | Pack et al. | |
| 4,567,880 A | 2/1986 | Goodman | |
| 4,578,060 A * | 3/1986 | Huck | A61M 1/0011 |
| | | | 604/133 |
| 4,589,414 A | 5/1986 | Yoshida et al. | |
| 4,601,284 A | 7/1986 | Arakawa et al. | |
| 4,601,290 A | 7/1986 | Effron et al. | |
| 4,606,330 A | 8/1986 | Bonnet | |
| 4,630,598 A | 12/1986 | Bonnet | |
| 4,642,088 A * | 2/1987 | Gunter | A61M 1/02 |
| | | | 604/319 |
| 4,644,952 A | 2/1987 | Patipa et al. | |
| 4,649,919 A | 3/1987 | Thimsen et al. | |
| 4,700,694 A | 10/1987 | Shishido | |
| 4,706,656 A | 11/1987 | Kuboto | |
| 4,718,291 A | 1/1988 | Wood et al. | |
| 4,737,142 A | 4/1988 | Heckele | |
| 4,749,376 A | 6/1988 | Kensey et al. | |
| 4,756,309 A | 7/1988 | Sachse et al. | |
| 4,819,635 A | 4/1989 | Shapiro | |
| 4,844,064 A | 7/1989 | Thimsen et al. | |
| 4,850,354 A | 7/1989 | McGurk-Burleson et al. | |
| 4,856,919 A | 8/1989 | Takeuchi et al. | |
| 4,867,157 A | 9/1989 | McGurk-Burleson et al. | |
| 4,924,851 A | 5/1990 | Ognier et al. | |
| 4,940,061 A | 7/1990 | Terwilliger et al. | |
| 4,950,278 A | 8/1990 | Sachse et al. | |
| 4,955,882 A | 9/1990 | Hakky | |
| 4,971,034 A | 11/1990 | Doi et al. | |
| 4,981,474 A * | 1/1991 | Bopp | A61M 1/0011 |
| | | | 600/580 |
| 4,986,827 A | 1/1991 | Akkas et al. | |
| 4,998,527 A | 3/1991 | Meyer | |
| 4,998,914 A | 3/1991 | Wiest et al. | |
| 5,007,917 A | 4/1991 | Evans | |
| 5,027,792 A | 7/1991 | Meyer | |
| 5,037,386 A | 8/1991 | Marcus et al. | |
| 5,105,800 A | 4/1992 | Takahashi et al. | |
| 5,106,364 A | 4/1992 | Hayafuji et al. | |
| 5,112,299 A | 5/1992 | Pascaloff | |
| 5,116,868 A | 5/1992 | Chen et al. | |
| 5,125,910 A | 6/1992 | Freitas | |
| 5,133,713 A | 7/1992 | Huang et al. | |
| 5,149,325 A * | 9/1992 | Telang | A61M 1/0013 |
| | | | 604/119 |
| 5,152,744 A | 10/1992 | Krause et al. | |
| 5,158,553 A | 10/1992 | Berry et al. | |
| 5,163,433 A | 11/1992 | Kagawa et al. | |
| 5,169,397 A | 12/1992 | Sakashita et al. | |
| 5,176,677 A | 1/1993 | Wuchinich | |
| 5,195,541 A | 3/1993 | Obenchain | |
| 5,226,910 A | 7/1993 | Kajiyama et al. | |
| 5,244,459 A | 9/1993 | Hill | |
| 5,254,117 A | 10/1993 | Rigby et al. | |
| 5,269,785 A | 12/1993 | Bonutti | |
| 5,270,622 A | 12/1993 | Krause | |
| 5,275,609 A | 1/1994 | Pingleton et al. | |
| 5,288,290 A | 2/1994 | Brody | |
| 5,304,118 A | 4/1994 | Trese et al. | |
| 5,312,399 A | 5/1994 | Hakky et al. | |
| 5,312,425 A | 5/1994 | Evans et al. | |
| 5,312,430 A | 5/1994 | Rosenbluth et al. | |
| 5,320,091 A | 6/1994 | Grossi et al. | |
| 5,347,992 A | 9/1994 | Pearlman et al. | |
| 5,350,390 A | 9/1994 | Sher | |
| 5,364,395 A | 11/1994 | West, Jr. | |
| 5,374,253 A | 12/1994 | Burns, Sr. et al. | |
| 5,390,585 A | 2/1995 | Ryuh | |
| 5,392,765 A | 2/1995 | Muller | |
| 5,395,313 A | 3/1995 | Naves et al. | |
| 5,403,276 A | 4/1995 | Schechter et al. | |
| 5,409,013 A | 4/1995 | Clement | |
| 5,409,453 A | 4/1995 | Lundquist et al. | |
| 5,411,513 A | 5/1995 | Ireland et al. | |
| 5,421,819 A | 6/1995 | Edwards et al. | |
| 5,425,376 A | 6/1995 | Banys et al. | |
| 5,429,601 A | 7/1995 | Conley et al. | |
| 5,435,805 A | 7/1995 | Edwards et al. | |
| 5,443,476 A | 8/1995 | Shapiro | |
| 5,449,356 A | 9/1995 | Walbrink et al. | |
| 5,451,218 A * | 9/1995 | Moore | A61M 25/0017 |
| | | | 604/317 |
| 5,456,673 A | 10/1995 | Ziegler et al. | |
| 5,456,689 A | 10/1995 | Kresch et al. | |
| 5,460,490 A | 10/1995 | Carr et al. | |
| 5,483,951 A | 1/1996 | Frassica et al. | |
| 5,490,819 A | 2/1996 | Nicholas et al. | |
| 5,490,860 A | 2/1996 | Middle et al. | |
| 5,492,537 A | 2/1996 | Vancaillie | |
| 5,498,258 A | 3/1996 | Hakky et al. | |
| 5,505,717 A * | 4/1996 | Moore | A61M 25/0017 |
| | | | 604/329 |
| 5,527,331 A | 6/1996 | Kresch et al. | |
| 5,549,541 A | 8/1996 | Muller | |
| 5,556,378 A | 9/1996 | Storz et al. | |
| 5,563,481 A | 10/1996 | Krause | |
| 5,569,164 A | 10/1996 | Lurz | |
| 5,569,254 A | 10/1996 | Carlson et al. | |
| 5,569,284 A | 10/1996 | Young et al. | |
| 5,575,756 A | 11/1996 | Karasawa et al. | |
| 5,586,973 A | 12/1996 | Lemaire et al. | |
| 5,591,187 A | 1/1997 | Dekel | |
| 5,601,583 A | 2/1997 | Donahue et al. | |
| 5,601,603 A | 2/1997 | Illi | |
| 5,602,449 A | 2/1997 | Krause et al. | |
| 5,603,332 A | 2/1997 | O'Connor | |
| 5,630,798 A | 5/1997 | Beiser et al. | |
| 5,649,547 A | 7/1997 | Ritchart et al. | |
| 5,669,927 A | 9/1997 | Boebel et al. | |
| 5,672,945 A | 9/1997 | Krause | |
| 5,674,179 A | 10/1997 | Bonnet et al. | |
| 5,676,497 A | 10/1997 | Kim | |
| 5,695,448 A | 12/1997 | Kimura et al. | |
| 5,702,420 A | 12/1997 | Sterling et al. | |
| 5,709,698 A | 1/1998 | Adams et al. | |

(56) References Cited

U.S. PATENT DOCUMENTS

| | | |
|---|---|---|
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,224,617 B1 | 5/2001 | Saadat et al. |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,597,662 B2 | 10/2009 | Litscher et al. |
| 7,763,033 B2 | 7/2010 | Gruber et al. |
| 7,922,737 B1 | 4/2011 | Cesarini et al. |
| 8,025,656 B2 | 9/2011 | Gruber et al. |
| 8,061,359 B2 | 11/2011 | Emanuel |
| 8,062,214 B2 | 11/2011 | Shener et al. |
| 8,419,626 B2 | 4/2013 | Shener-Irmakoglu et al. |
| 8,465,421 B2 | 6/2013 | Finkman et al. |
| 8,528,563 B2 | 9/2013 | Gruber |
| 8,540,656 B1 * | 9/2013 | Powlan ................ A61F 5/3761 602/36 |
| 8,574,253 B2 | 11/2013 | Gruber et al. |
| 8,647,349 B2 | 2/2014 | Gruber et al. |
| 8,663,264 B2 | 3/2014 | Cesarini et al. |
| 8,678,999 B2 | 3/2014 | Isaacson |
| 8,834,487 B2 | 9/2014 | Gruber et al. |
| 8,840,625 B2 | 9/2014 | Adams et al. |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,760 B2 | 6/2015 | Sullivan et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,095,366 B2 | 8/2015 | Sullivan et al. |
| 9,125,550 B2 | 9/2015 | Shener-Irmakoglu et al. |
| 9,155,454 B2 | 10/2015 | Sahney et al. |
| 9,259,233 B2 | 2/2016 | Gruber et al. |
| 9,581,942 B1 * | 2/2017 | Shippert ............. A61M 1/0056 |
| 9,943,639 B2 | 4/2018 | Germain et al. |
| 2001/0039963 A1 | 11/2001 | Spear |
| 2001/0047183 A1 | 11/2001 | Privitera |
| 2002/0058859 A1 | 5/2002 | Brommersma |
| 2002/0165427 A1 | 11/2002 | Yachia |
| 2003/0050603 A1 | 3/2003 | Todd |
| 2003/0050638 A1 | 3/2003 | Yachia |
| 2003/0078609 A1 | 4/2003 | Finlay |
| 2003/0114875 A1 | 6/2003 | Sjostrom |
| 2004/0204671 A1 | 10/2004 | Stubbs |
| 2005/0043690 A1 | 2/2005 | Todd |
| 2005/0085692 A1 | 4/2005 | Kiehn |
| 2006/0036132 A1 | 2/2006 | Renner |
| 2006/0047185 A1 | 3/2006 | Shener |
| 2006/0079853 A1 * | 4/2006 | Christensen ........ A61M 1/0023 604/317 |
| 2006/0241586 A1 | 10/2006 | Wilk |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams |
| 2008/0097469 A1 | 4/2008 | Gruber |
| 2008/0097470 A1 | 4/2008 | Gruber |
| 2008/0097471 A1 | 4/2008 | Adams |
| 2008/0135053 A1 | 6/2008 | Gruber |
| 2008/0146872 A1 | 6/2008 | Gruber |
| 2008/0146873 A1 | 6/2008 | Adams |
| 2008/0245371 A1 | 10/2008 | Gruber |
| 2008/0249366 A1 | 10/2008 | Gruber |
| 2008/0249534 A1 | 10/2008 | Gruber |
| 2008/0249553 A1 | 10/2008 | Gruber |
| 2008/0262308 A1 | 10/2008 | Prestezog |
| 2008/0300533 A1 * | 12/2008 | Lumpkin ............ A61M 1/0058 604/35 |
| 2009/0005747 A1 * | 1/2009 | Michaels ............... B65F 1/06 604/319 |
| 2009/0069763 A1 * | 3/2009 | DiCarlo ............... A61M 1/0011 604/328 |
| 2009/0082628 A1 | 3/2009 | Kucklick |
| 2009/0270812 A1 | 10/2009 | Litscher |
| 2009/0270895 A1 | 10/2009 | Churchill |

(56) References Cited

U.S. PATENT DOCUMENTS

| | | |
|---|---|---|
| 2009/0270896 A1 | 10/2009 | Sullivan |
| 2009/0270897 A1 | 10/2009 | Adams |
| 2009/0270898 A1 | 10/2009 | Chin |
| 2010/0030166 A1* | 2/2010 | Tout .................. A61M 1/90 604/316 |
| 2010/0087798 A1 | 4/2010 | Adams |
| 2010/0130957 A1* | 5/2010 | Smisson, III ....... A61M 1/3627 604/408 |
| 2010/0152647 A1 | 6/2010 | Shener |
| 2011/0034943 A1 | 2/2011 | Churchill |
| 2011/0077674 A1 | 3/2011 | Sullivan et al. |
| 2011/0118544 A1 | 5/2011 | Adams |
| 2011/0118680 A1* | 5/2011 | Michaels ............ A61M 1/0023 604/317 |
| 2011/0166419 A1 | 7/2011 | Reif |
| 2011/0290091 A1* | 12/2011 | Clark, II ............... B23D 21/14 83/54 |
| 2012/0067352 A1 | 3/2012 | Gruber |
| 2012/0078038 A1 | 3/2012 | Sahney |
| 2013/0131452 A1 | 5/2013 | Kuroda |
| 2014/0031834 A1 | 1/2014 | Germain |
| 2014/0142483 A1* | 5/2014 | Jackson, Jr. ............ A61F 5/013 602/16 |
| 2014/0276488 A1* | 9/2014 | Locke .................. A61M 1/98 604/319 |
| 2017/0172796 A1 | 6/2017 | Biancalana et al. |
| 2019/0365988 A1* | 12/2019 | Kim .................. A61M 5/1414 |

FOREIGN PATENT DOCUMENTS

| | | | |
|---|---|---|---|
| DE | 3601453 | A1 | 9/1986 |
| DE | 3615694 | A1 | 11/1987 |
| DE | 4038398 | A1 | 6/1992 |
| DE | 4440035 | A1 | 5/1996 |
| DE | 19633124 | A1 | 5/1997 |
| DE | 19751632 | C1 | 9/1999 |
| DE | 102006022827 | A1 | 12/2006 |
| EP | 0310285 | A2 | 4/1989 |
| EP | 0327410 | A1 | 8/1989 |
| EP | 0557044 | A1 | 8/1993 |
| EP | 0582295 | A2 | 2/1994 |
| EP | 0606531 | A2 | 7/1994 |
| EP | 0621008 | A2 | 10/1994 |
| EP | 0806183 | A1 | 11/1997 |
| EP | 1681022 | A1 | 7/2006 |
| GB | 2093353 | A | 9/1982 |
| GB | 2311468 | A | 10/1997 |
| JP | 2001075416 | A | 3/2001 |
| JP | 2002529185 | A | 9/2002 |
| JP | 2002538889 | A | 11/2002 |
| JP | 2003245247 | A | 9/2003 |
| NL | 1006944 | C2 | 3/1999 |
| WO | 8101648 | A1 | 6/1981 |
| WO | 9211816 | A2 | 7/1992 |
| WO | 9307821 | A1 | 4/1993 |
| WO | 9315664 | A1 | 8/1993 |
| WO | 9426181 | A1 | 11/1994 |
| WO | 9505777 | A1 | 3/1995 |
| WO | 9510981 | A1 | 4/1995 |
| WO | 9510982 | A1 | 4/1995 |
| WO | 9522935 | A1 | 8/1995 |
| WO | 9530377 | A1 | 11/1995 |
| WO | 9611638 | A1 | 4/1996 |
| WO | 9626676 | A1 | 9/1996 |
| WO | 9709922 | A1 | 3/1997 |
| WO | 9717027 | A1 | 5/1997 |
| WO | 9719642 | A1 | 6/1997 |
| WO | 9724071 | A1 | 7/1997 |
| WO | 9734534 | A1 | 9/1997 |
| WO | 9735522 | A1 | 10/1997 |
| WO | 9809569 | A1 | 3/1998 |
| WO | 9810707 | A1 | 3/1998 |
| WO | 9846147 | A1 | 10/1998 |
| WO | 9903407 | A1 | 1/1999 |
| WO | 9903409 | A1 | 1/1999 |
| WO | 9907295 | A1 | 2/1999 |
| WO | 9911184 | A1 | 3/1999 |
| WO | 9939648 | A1 | 8/1999 |
| WO | 9944506 | A1 | 9/1999 |
| WO | 9960935 | A1 | 12/1999 |
| WO | 0012010 | A1 | 3/2000 |
| WO | 0028890 | A1 | 5/2000 |
| WO | 0033743 | A1 | 6/2000 |
| WO | 0044295 | A1 | 8/2000 |
| WO | 0047116 | A1 | 8/2000 |
| WO | 0057797 | A1 | 10/2000 |
| WO | 0135831 | A1 | 5/2001 |
| WO | 0158368 | A1 | 8/2001 |
| WO | 0195810 | A2 | 12/2001 |
| WO | 02069808 | A2 | 9/2002 |
| WO | 03022164 | A1 | 3/2003 |
| WO | 03077767 | A1 | 9/2003 |
| WO | 2005060842 | A1 | 7/2005 |
| WO | 2005096963 | A2 | 10/2005 |
| WO | 2006105283 | A2 | 10/2006 |
| WO | 2006121968 | A2 | 11/2006 |
| WO | 2006121970 | A2 | 11/2006 |
| WO | 2007044833 | A2 | 4/2007 |
| WO | 2012044705 | A1 | 4/2012 |

* cited by examiner

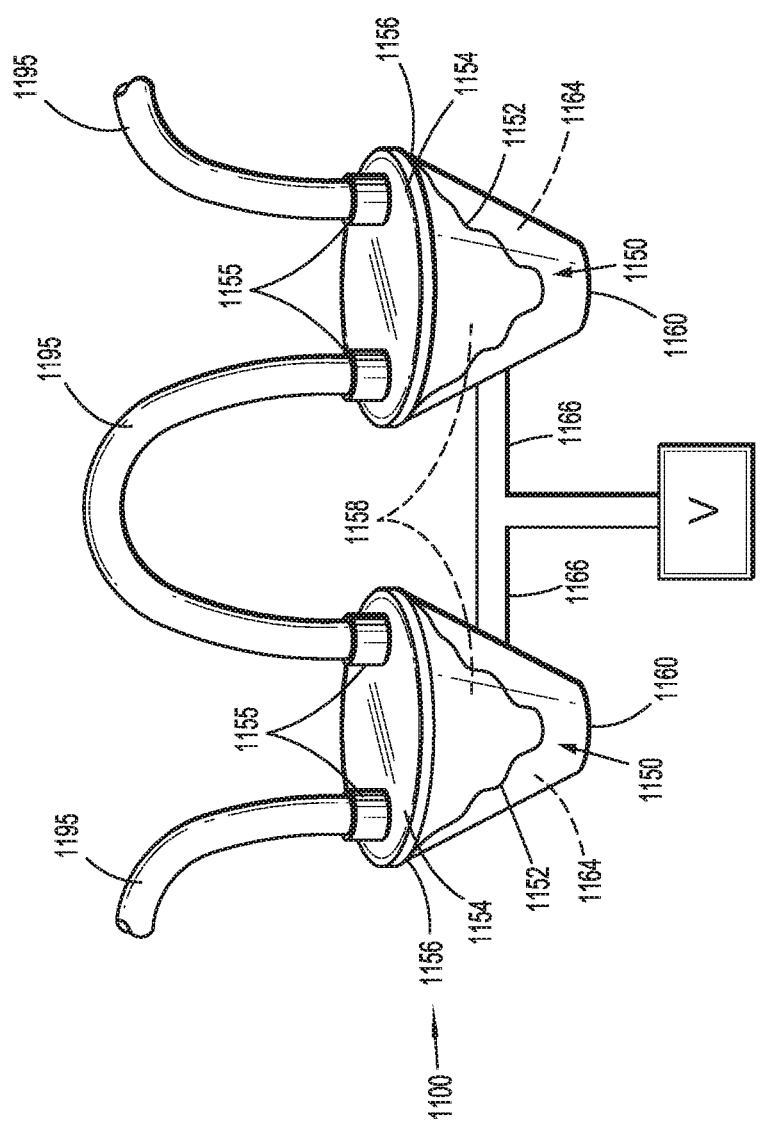

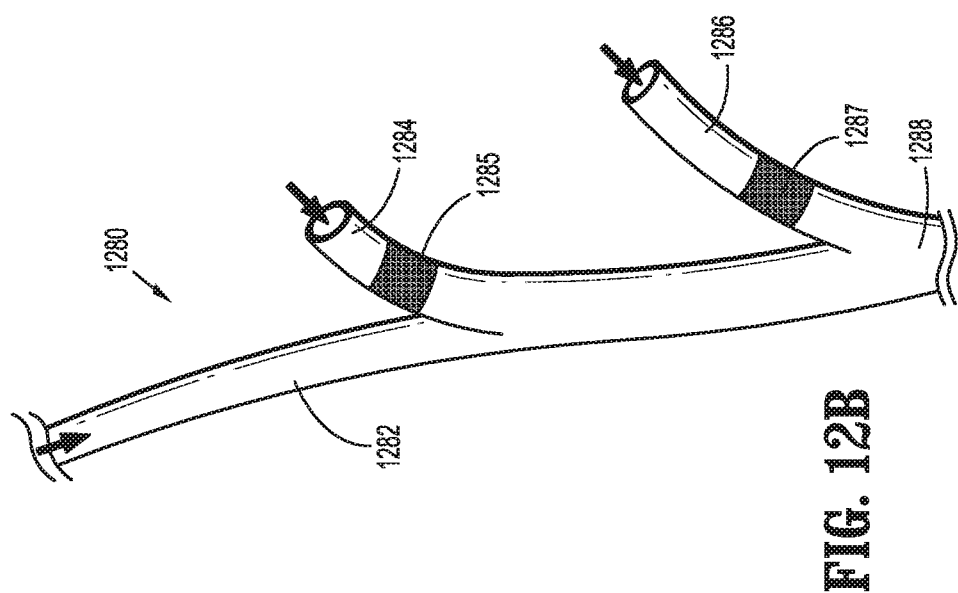
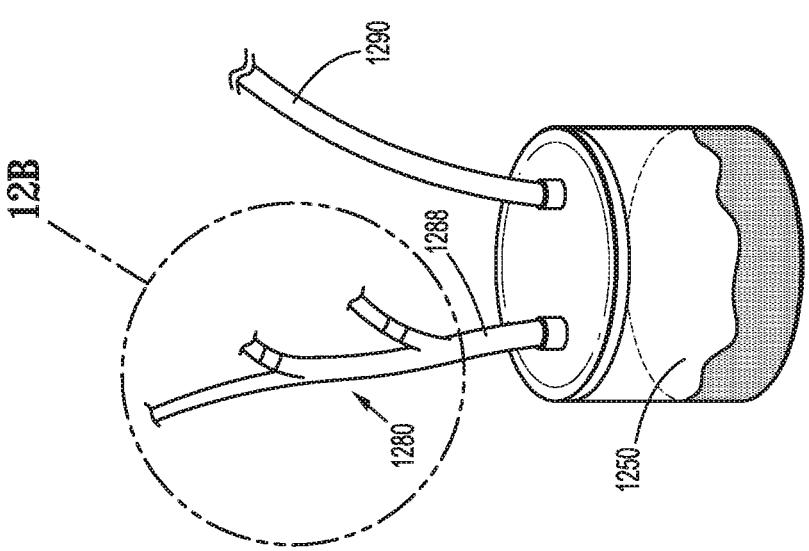

OUTFLOW COLLECTION VESSELS, SYSTEMS, AND COMPONENTS THEREOF FOR HYSTEROSCOPIC SURGICAL PROCEDURES

BACKGROUND

Technical Field

The present disclosure relates generally to surgical systems and, more particularly, outflow collection vessels, systems, and components thereof for hysteroscopic surgical procedures.

Background of Related Art

Surgical procedures, such as hysteroscopic surgical procedures, may be performed endoscopically within an organ, such as a uterus, by inserting an endoscope into the uterus and passing a tissue resection device through the endoscope and into the uterus. With respect to such hysteroscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space. The outflow fluid is collected by a collection system.

SUMMARY

As used herein, the term "distal" refers to the portion that is described which is further from a user, while the term "proximal" refers to the portion that is described which is closer to a user. Further, to the extent consistent, any or all of the aspects described herein may be used in conjunction with any or all of the other aspects described herein.

Provided in accordance with aspects of the present disclosure is a collection system for collecting outflow from a hysteroscopic surgical procedure. The collection system includes a collection vessel defining an internal volume and including a top portion and a bottom portion. The collection vessel is transitionable between a collapsed configuration and an expanded configuration. The collection system further includes a mounting stand including an upper retainer and a lower retainer. The upper retainer of the mounting stand is configured to retain the top portion of the collection vessel, e.g., at a top end of the collection vessel, on a side of the collection vessel towards the top end thereof, on a top or side of a plate attached to a top end of a body of the collection vessel, etc., and the lower retainer of the mounting stand is configured to retain the bottom portion of the collection vessel, e.g., at a lower end of the collection vessel, on a side of the collection vessel towards the lower end thereof, on a bottom or side of a plate attached to a lower end of a body of the collection vessel, etc. The upper and lower retainers are configured to retain the collection vessel thereon in the expanded configuration.

In an aspect of the present disclosure, the collection vessel includes a body and a top plate coupled to the body at the top portion of the collection vessel. In such aspects, the collection vessel may further include a bottom plate coupled to the body at the bottom end of the collection vessel.

In another aspect of the present disclosure, the top plate includes at least one port configured to connect to tubing such that the tubing is disposed in communication with the internal volume.

In yet another aspect of the present disclosure, the upper retainer includes at least one upper support arm configured to retain the top portion of the collection vessel thereon and the lower retainer includes at least one lower support arm configured to retain the bottom portion of the collection vessel thereon.

In still another aspect of the present disclosure, the top portion of the collection vessel defines at least one top eyelet configured to receive the at least one upper support arm and the bottom portion of the collection vessel defines at least one bottom eyelet configured to receive the at least one lower support arm.

In still yet another aspect of the present disclosure, the collection vessel includes a flexible body and a support frame supporting the flexible body in at least one of a radial direction or an axial direction. The support frame may include a helical wire that is selectively compressible in the axial direction, a plurality of support rings, and/or at least two frame components pivotably coupled to one another at the top and bottom portions of the collection vessel.

A surgical system provided in accordance with aspects of the present disclosure includes a surgical instrument, a vacuum pump, and a collection system for collecting outflow from the surgical instrument. The collection system includes a collection vessel defining an internal volume and including a top portion and a bottom portion. The collection vessel is transitionable between a collapsed configuration and an expanded configuration. The collection system further includes a mounting stand including an upper retainer and a lower retainer. The upper retainer is configured to retain the top portion of the collection vessel and the lower retainer is configured to retain the bottom portion of the collection vessel. The upper and lower retainers are configured to retain the collection vessel thereon in the expanded configuration. The collection system additionally includes outflow tubing connecting the surgical instrument with the internal volume of the collection vessel and vacuum tubing connecting the vacuum pump with the internal volume of the collection vessel.

In an aspect of the present disclosure, the collection vessel includes a body and a top plate coupled to the body at the top portion of the collection vessel.

In another aspect of the present disclosure, the top plate includes first and second ports to connect the outflow tubing and the vacuum tubing to the internal volume of the collection vessel.

In still another aspect of the present disclosure, the upper retainer includes at least one upper support arm configured to retain the top portion of the collection vessel thereon and the lower retainer includes at least one lower support arm configured to retain the bottom portion of the collection vessel thereon. The top portion of the collection vessel, in such aspects, may define at least one top eyelet configured to receive the at least one upper support arm and/or the bottom portion of the collection vessel may define at least one bottom eyelet configured to receive the at least one lower support arm.

In yet another aspect of the present disclosure, the collection vessel includes a flexible body and a support frame supporting the flexible body in at least one of a radial direction or an axial direction. The support frame may be configured to at least one of telescope, pivot, flex (e.g., compress and/or expand), or tilt to transition the collection vessel between the collapsed configuration and the expanded configuration.

In still yet another aspect of the present disclosure, the surgical instrument is a tissue resection instrument configured to receive outflow from a surgical site. In such aspects, the surgical system may further include a control console configured to control the tissue resection instrument. The control console may include the vacuum pump disposed therein.

Another collection system for collecting outflow from a hysteroscopic surgical procedure provided in accordance with the present disclosure includes a plurality of collection vessels, connection tubing, outflow tubing, and a plurality of retention canisters. Each collection vessel includes a flexible body defining an internal volume and transitionable between a collapsed configuration and an expanded configuration. The connection tubing couples adjacent collection vessels with one another and the outflow tubing is coupled to at least one of the collection vessels. Each retention canister includes a rigid body. Each collection vessel is configured to engage a corresponding retention canister such that each rigid body at least partially receives one of the flexible bodies therein.

In an aspect of the present disclosure, the connection tubing permanently couples the adjacent collection vessels.

In another aspect of the present disclosure, each collection vessel further includes a top plate disposed at an upper end of the flexible body. In aspects, the top plate includes at least one engagement finger configured to engage the rigid body of the corresponding retention canister. Alternatively or additionally, each top plate includes a gasket configured to sealingly engage the rigid body of the corresponding retention canister.

In still another aspect of the present disclosure, each rigid body defines an interior volume and vacuum tubing is coupled to each rigid body. The vacuum tubing is adapted to connect to a vacuum source to establish vacuum within the interior volumes of the rigid bodies, thereby establishing vacuum within the interior volumes of the flexible bodies.

In yet another aspect of the present disclosure, vacuum tubing is coupled to at least one of the flexible bodies and adapted to connect to a vacuum source such that, via the vacuum tubing and the connection tubing, vacuum is established within the interior volumes of the flexible bodies.

In still yet another aspect of the present disclosure, the plurality of collection vessels and the connection tubing are disposable after a single use and/or the plurality of retention canisters are reusable for multiple uses.

Another surgical system provided in accordance with the present disclosure includes a plurality of surgical components, a collection vessel, and outflow tubing including a base portion and a plurality of branches extending from the base portion. The base portion is configured to connect to the collection vessel and each branch is configured to connect to one of the surgical components. The system further includes a flow restrictor disposed within at least one (or all) of the branches.

In aspects of the present disclosure, the plurality of surgical components includes a surgical instrument, e.g., a tissue resection instrument, a surgical drape, and/or a hysteroscope.

In another aspect of the present disclosure, the system further includes a vacuum pump and vacuum tubing coupling the vacuum pump with the collection vessel to thereby establish suction through each branch of the plurality of branches of the outflow tubing.

In another aspect of the present disclosure, the system further includes a control console configured to control at least one surgical component of the plurality of surgical components. The control console may include the vacuum pump disposed therein.

BRIEF DESCRIPTION OF THE DRAWINGS

Various aspects and features of the present disclosure are described hereinbelow with reference to the drawings wherein like numerals designate identical or corresponding elements in each of the several views.

FIG. 11 is a perspective view of yet another collection system provided in accordance with the present disclosure and configured for use with the surgical system of FIG. 1; and FIG. 12A is a perspective view of still another collection system provided in accordance with the present disclosure and configured for use with the surgical system of FIG. 1; and FIG. 12B is an enlarged view of the area of detail indicated as "12B" in FIG. 12A.

DETAILED DESCRIPTION

Figure 1:
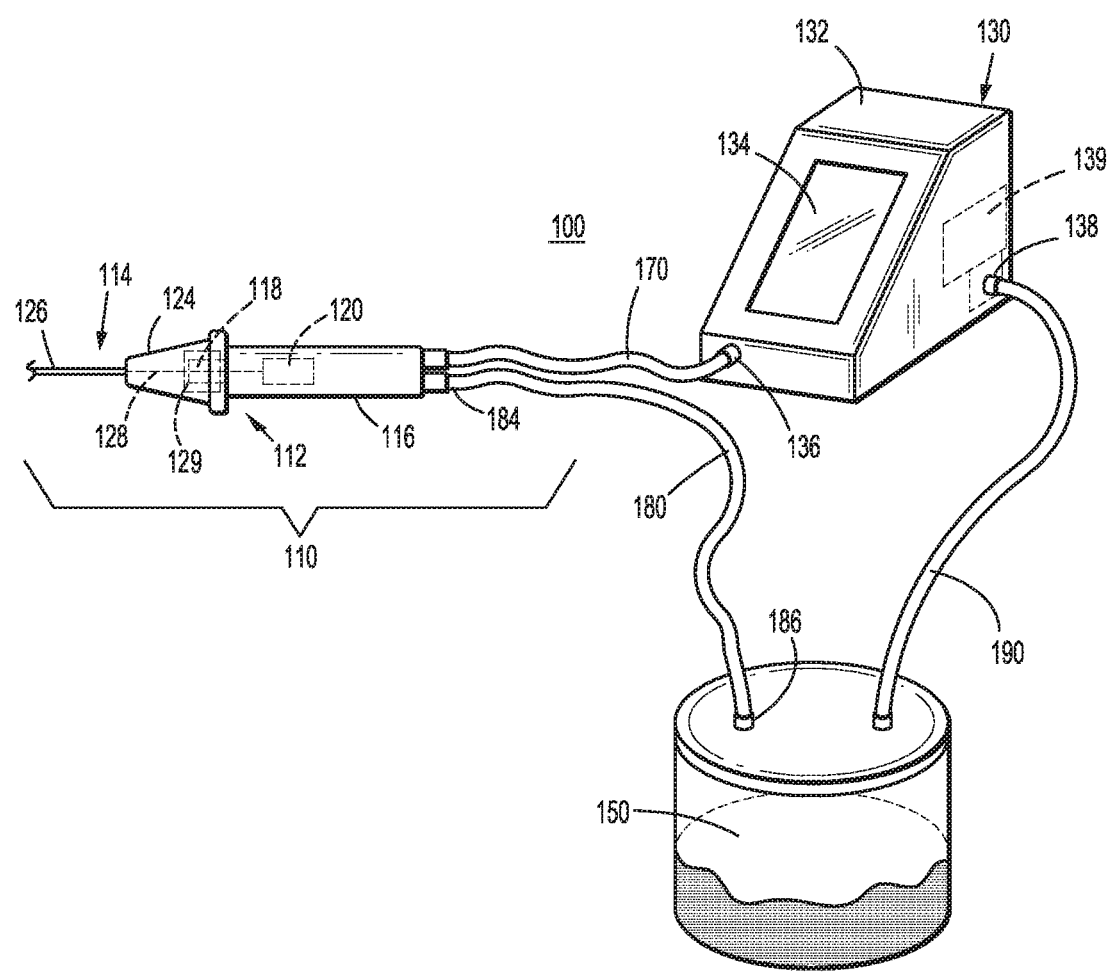
FIG. 1 is a perspective view of a surgical system configured for use in a hysteroscopic surgical procedure.

Referring to FIG. 1, a surgical system provided in accordance with aspects of the present disclosure is shown generally identified by reference numeral 100. Surgical system 100 includes a surgical instrument 110, a control console 130, and a collection vessel 150. Surgical system 100 further includes a cable 170, outflow tubing 180, and vacuum tubing 190. Surgical system 100 may further include an endoscope (not shown), e.g., a hysteroscope, defining a working channel for inserting of surgical instrument 110 therethrough, and adapted to connect to inflow tubing (not shown) to supply fluid to an internal surgical site and/or additional outflow tubing (not shown) to return fluid to collection vessel 150.

Surgical instrument 110 includes a handpiece 112 that may be configured as a reusable component and an end effector assembly 114 that may be configured as a single-use, disposable component. Handpiece 112 includes a housing 116 to facilitate grasping and manipulation of surgical instrument 110 by a user. Handpiece 112 further includes an output coupler 118 configured to operably engage end effector assembly 114, a motor 120 disposed within housing 116 and operably coupled to output coupler 118 to drive output coupler 118 and, thus, drive end effector assembly 114. Cable 170 electrically couples handpiece 112 and control console 130 with one another and, more specifically, electrically couples control console 130 with motor 120 to power and control operation of motor 120 and electrically couples control console 130 with a storage device(s), e.g., a microchip(s) (not explicitly shown), associated with handpiece 112 and/or end effector assembly 114 to enable communication of, for example, identification, setting, and control information therebetween. In embodiments, cable 170 is fixedly attached to handpiece 112 and releasably couplable with control console 130, although other configurations are also contemplated.

Continuing with reference to FIG. 1, end effector assembly 114 includes a proximal hub 124 configured to releasably engage housing 116 of handpiece 112 to releasably mechanically engage end effector assembly 114 with handpiece 112. End effector assembly 114 further includes an outer shaft 126 extending distally from proximal hub 124 and a cutting shaft 128 extending through outer shaft 126. A proximal end of cutting shaft 128 extends into proximal hub 124 wherein an input coupler 129 is engaged with cutting shaft 128. Input coupler 129 is configured to operably couple to output coupler 118 of handpiece 112 when proximal hub 124 is engaged with housing 116 such that, when motor 120 is activated to drive output coupler 118, input coupler 129 is driven in a corresponding manner to thereby move cutting shaft 128 within and relative to outer shaft 126.

Outer shaft 126, as noted above, extends distally from proximal hub 124 and, in embodiments, is stationary relative to proximal hub 124, although other configurations are also contemplated. Outer shaft 126 may define a window (not shown) through a side wall thereof towards a distal end thereof to provide access to cutting shaft 128 which is rotatably and/or translatably disposed within outer shaft 126. Cutting shaft 128 may define an opening (not shown) towards the distal end thereof providing access to the interior thereof and may include a serrated cutting edge (not shown) surrounding the opening, although other suitable cutting edge configurations are also contemplated. Alternatively, or additionally, outer shaft 126 may include a cutting edge defined about the window thereof.

Motor 120, as noted above, is activated to move cutting shaft 128 and, more specifically, to drive rotation and/or translation of cutting shaft 128 relative to outer shaft 126. Control console 130, coupled to motor 120 via cable 170, enables selective powering and controlling of motor 120 and, thus, selective rotation and/or translation of cutting shaft 128 relative to outer shaft 126 to resect tissue adjacent the distal end of end effector assembly 114. Control console 130 is detailed below.

Outflow tubing 180 includes a distal end 184 configured to releasably couple to handpiece 112 and a proximal end 186 configured to couple to collection vessel 150. More specifically, handpiece 112 defines an internal passage (not shown) that couples distal end 184 of outflow tubing 180 with the interior of cutting shaft 128 in fluid communication with the interior of cutting shaft 128 such that fluid, tissue, and debris drawn into cutting shaft 128 and/or outer shaft 126 may be suctioned, under vacuum, e.g., from vacuum pump 139 of control console 130, through end effector assembly 114, handpiece 112, and outflow tubing 180 to collection vessel 150.

Referring still to FIG. 1, collection vessel 150, as noted above, is coupled to proximal end 186 of outflow tubing 180 to receive the fluid, tissue, and debris suctioned through end effector assembly 114 and outflow tubing 180. Vacuum tubing 190 is coupled between collection vessel 150 and a vacuum source, e.g., vacuum pump 139 of control console 130, such that, upon activation of vacuum pump 139, negative pressure is established through collection vessel 150, outflow tubing 180, and the interior of cutting shaft 128 of end effector assembly 114 to draw the fluids, tissue, and debris into and through cutting shaft 128, handpiece 112, outflow tubing 180, and into collection vessel 150.

Control console 130 generally includes an outer housing 132, a touch-screen display 134 accessible from the exterior of outer housing 132, a cable port 136 configured to receive cable 170, a vacuum tubing port 138 configured to receive vacuum tubing 190, and a vacuum pump 139 disposed within outer housing 132 and operably coupled with vacuum port 138. Outer housing 132 further houses internal electronics (not shown) of control console 130. Control console 130 may be configured to connect to a mains power supply (not shown) for powering control console 130. Further, control console 130 may be configured to receive user input, e.g., use information, setting selections, etc., via touch-screen display 134 or a peripheral input device (not shown) coupled to control console 130. Operational input, e.g., ON/OFF signals, power level settings (HI power vs. LO power), etc., may likewise be input via touch-screen display 134 or a peripheral input device (not shown) such as, for example, a footswitch (not shown), a handswitch (not shown) disposed on handpiece 112, etc.

In use, upon an activation input provided to control console 130, control console 130 powers and controls motor 120 of handpiece 112 to, in turn, drive cutting shaft 128 of end effector assembly 114 to resect tissue adjacent the distal end of end effector assembly 114, while vacuum pump 139 of control console 130 suctions fluid, the resected tissue, and debris through cutting shaft 128, handpiece 112, outflow tubing 180, and into collection vessel 150.

Turning to FIGS. 2A-11, collection vessel 150 (FIG. 1) may define various different configurations and/or may be utilized with various different components to define a collection system. Such collection vessels and systems are provided in accordance with the present disclosure and detailed below with reference to FIGS. 2A-11. As an alternative to use with surgical system 100, the collection vessels and systems of the present disclosure may be utilized within any other suitable surgical system.

Figure 2B:
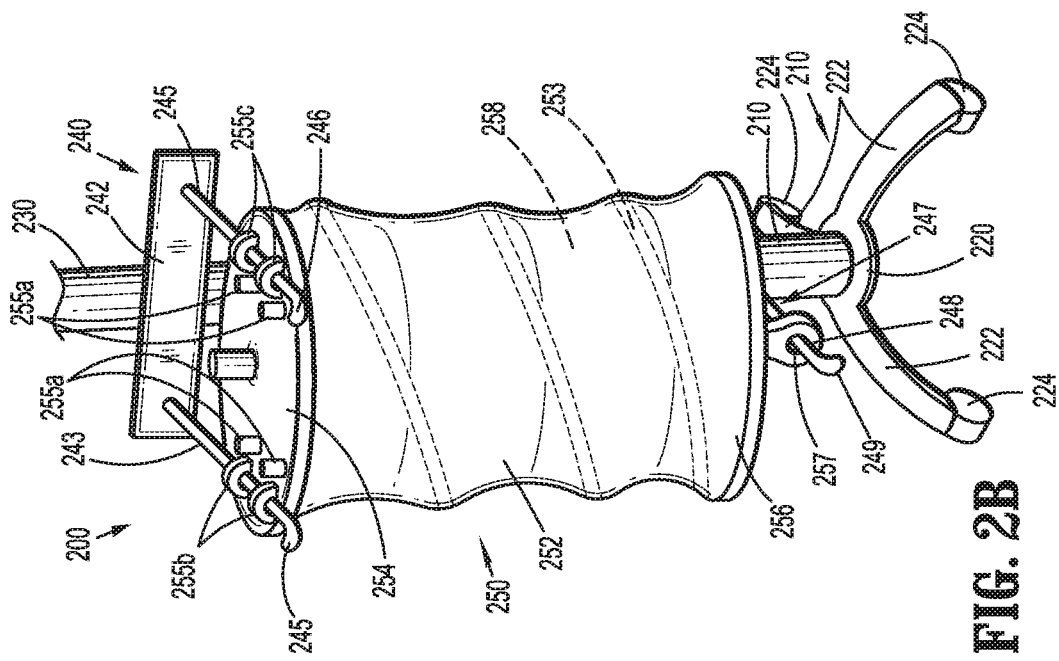
FIG. 2B is a perspective view of the collection system of FIG. 2A, disposed in a use condition.
Figure 2A:
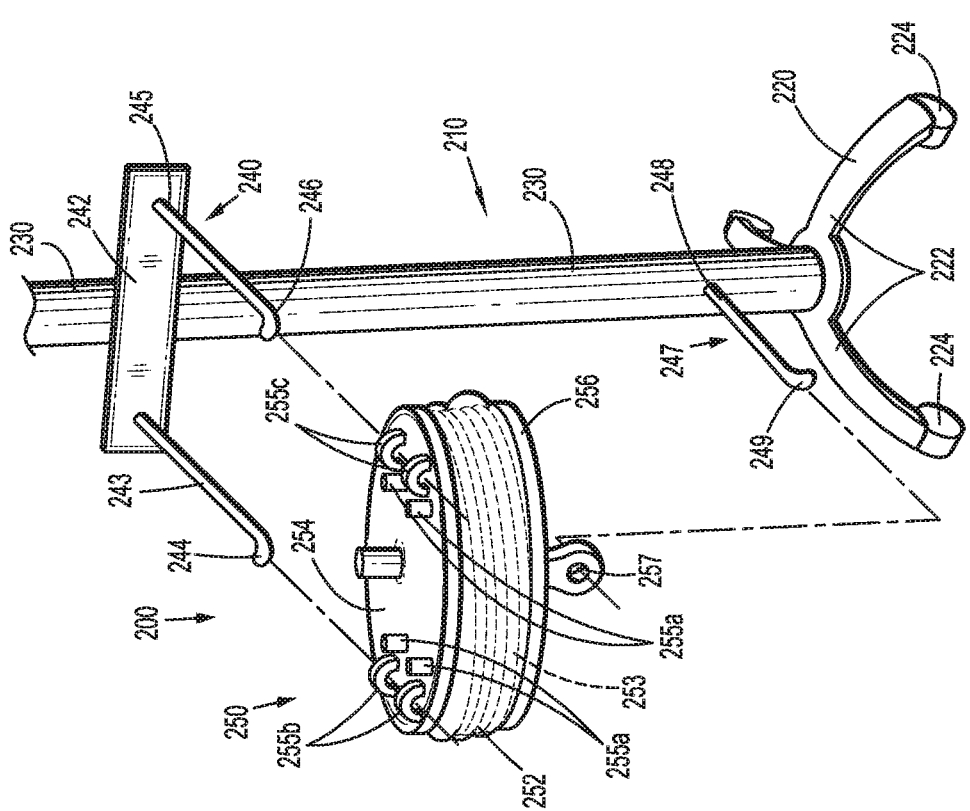
FIG. 2A is a perspective view of a collection system provided in accordance with the present disclosure and configured for use with the surgical system of FIG. 1, wherein the collection system is disposed in a storage condition.

With reference to FIGS. 2A and 2B, a collection system 200 provided in accordance with the present disclosure includes a mounting stand 210 and a collection vessel 250.

Mounting stand 210 includes a base 220, a vertical support 230, an upper vessel retainer 240 and a lower vessel retainer 247. Base 220 may include one or more feet 222, e.g., three feet defining a tripod configuration, each supporting a caster 224 thereon to facilitate rolling mounting stand 210 along a surface, e.g., the floor. Casters 224 may be selectively lockable to fix mounting stand 210 in position on the surface.

Vertical support 230 is fixed relative to and extends upwardly from base 220. Vertical support 230 may be configured as a cylindrical pole or may define any other suitable configuration providing one or more vertically-extending structures.

Upper vessel retainer 240 includes a crossbar 242 mounted on vertical support 230. Crossbar 242 may be mounted on vertical support 230 via a releasable locking mechanism, e.g., a clamp (not shown), to enable sliding of crossbar 242 vertically along vertical support 230 to a desired position and locking of crossbar 242 in the desired position, e.g., via tightening the clamp. A pair of spaced-apart support arms 243, 245 extend from crossbar 242 in generally perpendicular orientation relative to vertical support 230. Support arms 243, 245 include retention features 244, 246, respectively, at the free ends thereof. Retention features 244, 246 may include inclined segments, hooks, tortuous segments, and/or other suitable features configured to inhibit components supported by support arms 243, 245 from slipping off the free ends thereof.

Lower vessel retainer 247 includes a support arm 248 mounted on and extending from vertical support 230 in generally perpendicular orientation relative to vertical support 230. Alternatively, support arm 248 may extend from a crossbar (e.g., similar to crossbar 242) coupled to vertical support 230 via a releasable locking mechanism. Support arm 248 includes a retention feature 249 at the free end thereof, e.g., an inclined segment, hook, tortuous segment, and/or other suitable feature, configured to inhibit components supported by support arm 248 from slipping off the free end thereof.

Continuing with reference to FIGS. 2A and 2B, collection vessel 250 includes a body 252, a top plate 254, and a bottom plate 256 that cooperate to define an interior volume 258 of collection vessel 250. Collection vessel 250 further includes a structural frame 253. Body 252 of collection vessel 250 defines a generally cylindrical configuration and is formed from one or more layers of a flexible material suitable for retaining surgical fluids, e.g., PVC, polypropylene, ethylene vinyl acetate, etc. In embodiments, body 252 is optically transparent to enable visualization therethrough and into interior volume 258. The flexibility of body 252 enables body 252 to be transitioned between a storage condition, wherein body 252 is collapsed longitudinally to define a reduced height, and a use condition, wherein body 252 is expanded longitudinally to define an increased height. In embodiments, the diameter of body 252 remains substantially constant regardless of whether body 252 is disposed in the storage condition or the use condition.

Top plate 254 is sealed to the top end of body 252 about the annular perimeter of body 252, e.g., using an adhesive, via heat sealing, or in any other suitable manner, to create a fluid-tight seal at the top end of interior volume 258 of collection vessel 250. Top plate 254 is formed from a rigid or semi-rigid material and defines a disc-shaped configuration although other configurations are also contemplated. Top plate 254 includes a plurality of ports 255a defined therethrough, one or more first eyelets 255b and one or more second eyelets 255c. The plurality of ports 255a enable connection of various tubing to collection vessel 250 in fluid communication with interior volume 258. For example: outflow tubing 180 (FIG. 1) may be connected to one of the ports 255a to enable fluid, tissue, and debris removed from a surgical site to be deposited into interior volume 258; vacuum tubing 190 (FIG. 1) may be connected to one of the ports 255a to generate vacuum within interior volume 258 for drawing fluid, tissue, and debris through outflow tubing 180 (FIG. 1) and into interior volume 258; and/or connection tubing (not shown) may be connected to one of the ports 255a to connect collection vessel 250 to an additional collection vessel(s) to enable fluid, tissue, and debris to fill the additional collection vessels(s) during use. Ports 255a may include one-way valves, other suitable valves, and/or caps to enable selective sealing of posts 255a in a closed condition.

The one or more first eyelets 255b of top plate 254 may be formed from hooks (closed or open), arches, key heads, or other suitable structures disposed on top plate 254. In embodiments, at least two first eyelets 255b are provided wherein the at least two first eyelets 255b are spaced-apart from and aligned with one another. The one or more second eyelets 255c of top plate 254 may be formed from hooks (closed or open), arches, key heads, or other suitable structures disposed on top plate 254. In embodiments, at least two second eyelets 255c are provided wherein the at least two second eyelets 255c are spaced-apart from and aligned with one another. Further, the first and second eyelets 255b, 255c, respectively, are spaced-apart from one another and, in embodiments where multiple first and second eyelets 255b, 255c, respectively, are provided, the alignment axes thereof are disposed in parallel orientation relative to one another.

The one or more first eyelets 255b of top plate 254 are configured to receive support arm 243 therethrough while the one or more second eyelets 255c of top plate 254 are configured to receive support arm 245 therethrough to mount collection vessel 250 on mounting stand 210 suspended from upper vessel retainer 240. Retention features 244, 246 help maintain top plate 254 suspended from arms 243, 245.

Bottom plate 256 is sealed to the bottom end of body 252 about the annular perimeter of body 252, e.g., using an adhesive, via heat sealing, or in any other suitable manner, to create a fluid-tight seal at the bottom end of interior volume 258 of collection vessel 250 such that, body 252, top plate 254, and bottom plate 256 cooperate to define a sealed interior volume 258. Bottom plate 256 is formed from a rigid or semi-rigid material and defines a disc-shaped configuration although other configurations are also contemplated. Bottom plate 256 includes one or more eyelets 257, e.g., formed from a hook (closed or open), arch, key head, or other suitable structure disposed on bottom plate 256. The one or more eyelets 257 of bottom plate 256 are configured to receive support arm 248 therethrough to retain bottom plate 256 in spaced-apart position relative to top plate 254 and, thus, to retain collection vessel 250 on mounting stand 210 in the use condition wherein collection vessel 250 is longitudinally expanded. Retaining collection vessel 250 in the use condition is important to maintain interior volume 258 when vacuum is applied therein, thus permitting depositing of fluid, tissue, and debris therein. Without such retention, due to the flexibility of collection vessel 250, collection vessel 250 would collapse down to the storage condition upon application of vacuum to interior volume 258. Thus, collection vessel 250 may assume a low-profile storage configuration to facilitate storage, transportation, etc., while mounting stand 210 maintains collection vessel 250 in an expanded configuration during use to not compromise functionality.

Structural frame 253 of collection vessel 250 is disposed within or between the one or more layers of material forming body 252 and provides radial structural support to collection vessel 250, e.g., inhibiting radial inward collapse of body 252. Structural frame 253 may be formed from one or more pieces of wire defining one or more helixes. The helical configuration of structural frame 253 provides the above-mentioned radial structural support while allowing expansion and collapse of structural frame 253 (via increasing and decreasing, respectively, the pitch of the helix of structural frame 253) to accommodate transitioning of collection vessel 250 between the storage and use conditions.

In embodiments, collection system 200 includes a plurality of pairs of upper vessel retainers 240 and lower vessel retainers 247 stacked vertically along a portion of the length of vertical support 230 and/or disposed radially about vertical support 230 to enable mounting of plural collection vessels 250 on mounting stand 210.

Figure 3:
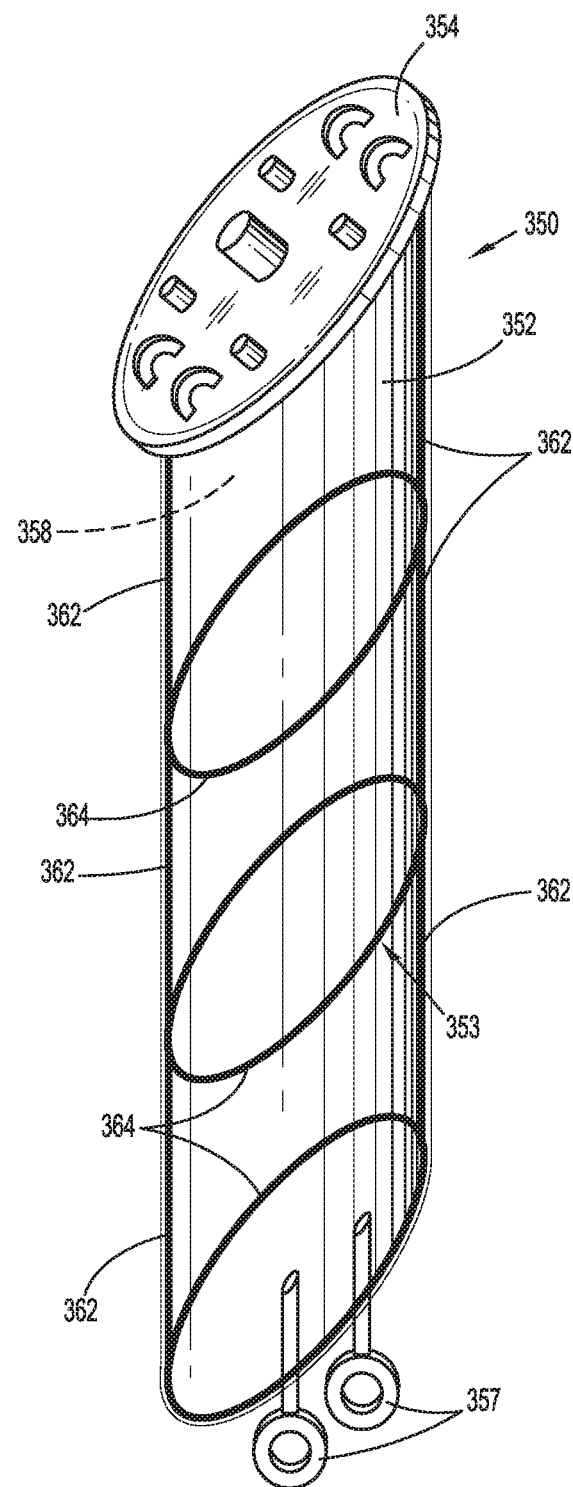
FIG. 3 is a perspective view of another collection vessel configured for use with the collection system of FIG. 2A.

With reference to FIG. 3, another collection vessel provided in accordance with the present disclosure is shown generally identified by reference numeral 350. Collection vessel 350 is similar to and may include any of the features of collection vessel 250 (FIGS. 2A and 2B), expect as specifically contradicted below. Further, collection vessel 350 may be configured for use with a collection system e.g., collection system 200 (FIGS. 2A and 2B) or other suitable collection system, and/or a surgical system, e.g., surgical system 100 (FIG. 1) or any other suitable surgical system.

Collection vessel 350 includes a body 352 defining a closed bottom end and an open top end and a top plate 354 sealed to the open top end of body 352 about the annular perimeter of body 352 to seal the interior volume 358 of collection vessel 350. As an alternative to body 352 having a closed bottom end, a bottom plate may be provided similarly as detailed above with respect to collection vessel 250 (FIGS. 2A and 2B).

Collection vessel 350 further includes a structural frame 353 including a plurality of pairs of axial supports 362 disposed within or between the one or more layers of material forming body 352 and a plurality of ring supports 364 disposed within or between the one or more layers of material forming body 352. Axial supports 362 and ring supports 364 may each be formed from one or more piece of wire. Ring supports 364 are longitudinally-spaced along at least a portion of the length of body 352 while each pair of axial supports 362 extends longitudinally between an adjacent pair of ring supports 364 and includes first and second diametrically opposed axial supports 362. Ring supports 364 and axial supports 362 may be separate from one another to enable collapsing, folding, and/or rolling of body 352 to achieve the storage condition thereof, or may be coupled to one another via living hinges or other suitable joints to enable collapsing, folding, and/or rolling of body 352 to achieve the storage condition. In other embodiments, ring supports 364 and axial supports 362 are releasably connected to one another.

In embodiments where body 352 has a closed bottom end and a bottom plate is not provided, the structure(s) defining the one or more bottom eyelets 357 of collection vessel 350 may be connected to body 352, the bottom-most axial support(s) 362, and/or the bottom-most ring support 364, either directly or indirectly, e.g., via additional framing or other structure(s). Alternatively, bottom eyelets 357 may be omitted and axial supports 362 relied upon to provide the longitudinal structural support to collection vessel 350.

Figure 4B:
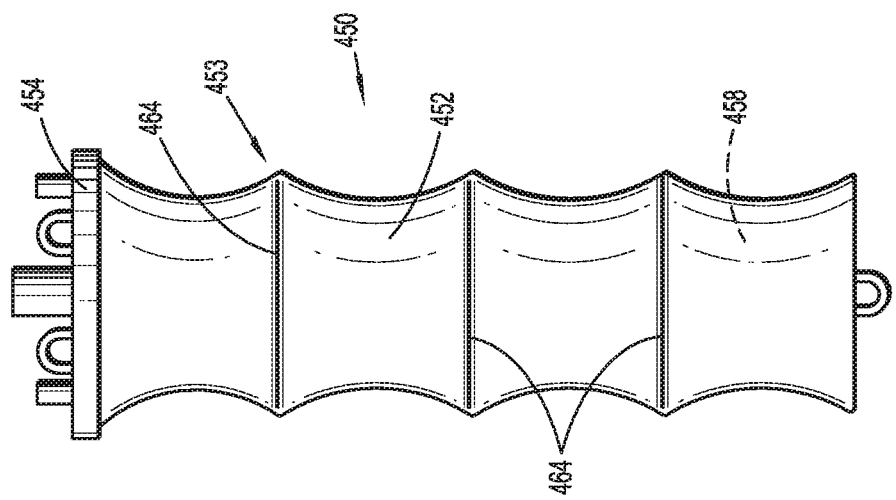
FIG. 4B is a side view of the collection vessel of FIG. 4A.
Figure 4A:
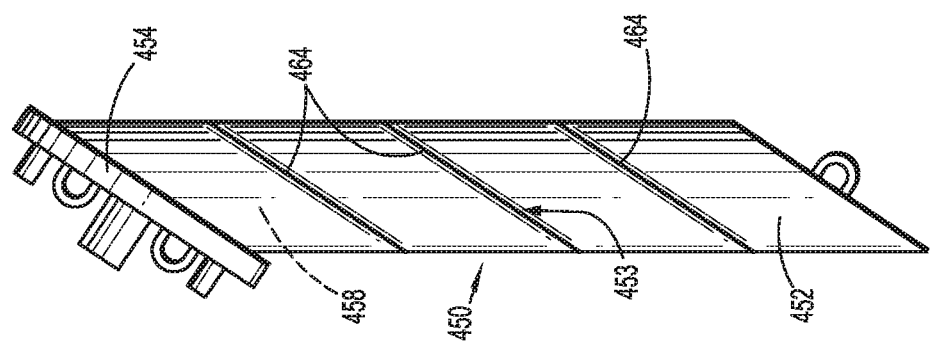
FIG. 4A is a perspective view of still another collection vessel configured for use with the collection system of FIG. 2A.

Referring to FIGS. 4A and 4B, another collection vessel provided in accordance with the present disclosure is shown generally identified by reference numeral 450. Collection vessel 450 is similar to and may include any of the features of collection vessels 250 (FIGS. 2A and 2B), 350 (FIG. 3), expect as specifically contradicted below. Further, collection vessel 450 may be configured for use with a collection system e.g., collection system 200 (FIGS. 2A and 2B) or other suitable collection system, and/or a surgical system, e.g., surgical system 100 (FIG. 1) or any other suitable surgical system.

Collection vessel 450 includes a body 452 defining a closed bottom end and an open top end, a top plate 454 sealed to the open top end of body 452 about the annular perimeter of body 452 to seal the interior volume 458 of collection vessel 450. As an alternative to body 452 having a closed bottom end, a bottom plate may be provided similarly as detailed above with respect to collection vessel 250 (FIGS. 2A and 2B).

Collection vessel 450 further includes a structural frame 453 including a plurality of ring supports 464 disposed within or between the one or more layers of material forming body 452 and longitudinally-spaced along at least a portion of the length of body 452. Each ring support 464 may be formed from one or more pieces of wire. Some or all of the ring supports 464 may define a floating configuration wherein such ring supports 464 are not rigidly connected to any other structure. In this manner collection vessel 450 is provided with radial rigidity via ring supports 464 but is longitudinally flexible, enabling collapse and expansion of body 452.

In embodiments, top plate 454 may be tilted from a substantially perpendicular orientation relative to the longitudinal axis of body 452 (the use condition of collection vessel 450 (FIG. 4B)) to thereby tilt ring supports 464 in a similar manner. More specifically, top plate 454 and ring supports 464 may be tilted to achieve a substantially parallel orientation, e.g., within 15 degrees, relative to the longitudinal axis of body 452 such that collection vessel 450 defines a substantially flat configuration (the storage condition of collection vessel 450 (FIG. 4A)). The substantially flat collection vessel 450 may also be folded to further reduce the dimensions thereof in the storage condition. Collection vessel 450 may initially be provided, e.g., packaged at manufacturing, in the storage condition (FIG. 4A) and may then be expanded to the use condition (FIG. 4B) prior to use by tilting top plate 454 from the substantially parallel orientation to the substantially perpendicular orientation.

In embodiments where a bottom plate is provided, the bottom plate may be tilted between the storage and use conditions similarly as detailed above with respect to top plate 454. Additionally or alternatively, structure(s) defining eyelets at the bottom of collection vessel 450 may be connected to the bottom plate (where provided) to a bottom-most ring support 464, or to body 452, directly or indirectly, e.g., via additional framing or other structure(s).

Turning to FIGS. 5A-6B, another collection vessel provided in accordance with the present disclosure is shown generally identified by reference numeral 550. Collection vessel 550 is similar to and may include any of the features of collection vessels 250 (FIGS. 2A and 2B), 350 (FIG. 3), 450 (FIGS. 4A and 4B), expect as specifically contradicted below. Further, collection vessel 550 may be configured for use with a collection system e.g., collection system 200 (FIGS. 2A and 2B) or other suitable collection system, and/or a surgical system, e.g., surgical system 100 (FIG. 1) or any other suitable surgical system.

Collection vessel 550 includes a body 552 defining closed bottom and top ends to define a sealed interior volume 558, and a structural frame 553 disposed within or between the one or more layers of material forming body 552.

Figure 5A:
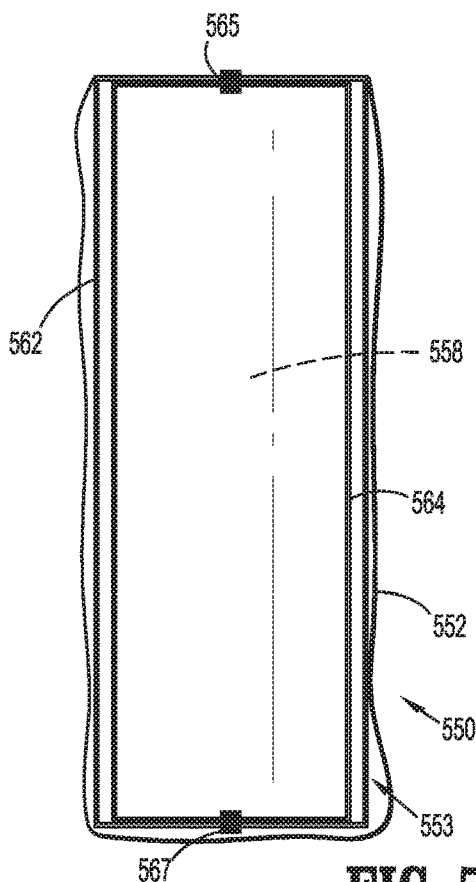
FIG. 5A is a side view of still another collection vessel configured for use with the collection system of FIG. 2A, disposed in a storage condition.
Figure 6A:
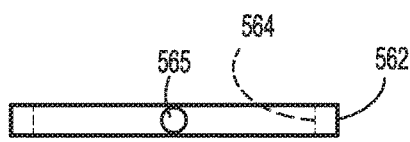
FIG. 6A is a top view of the collection vessel of FIG. 5A, disposed in the storage condition.
Figure 5B:
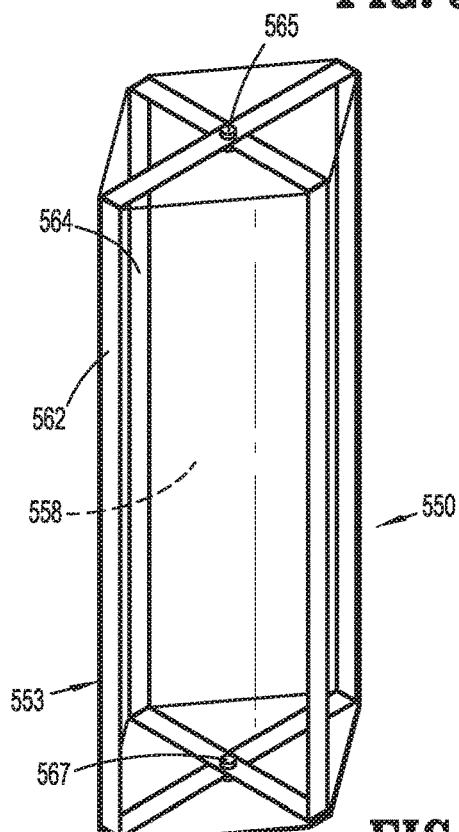
FIG. 5B is a perspective view of the collection vessel of FIG. 5A, disposed in a use condition.
Figure 6B:
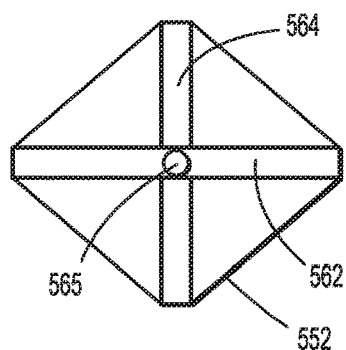
FIG. 6B is a top view of the collection vessel of FIG. 5A, disposed in the use condition.

Structural frame 553 includes a pair of rectangular frame components 562, 564 each defining a pair of opposed relatively long sides and a pair of opposed relatively short ends, although square configurations, oval-shaped configurations, or other suitable configurations are also contemplated. The top ends of frames 562 are pivotably coupled to one another about a pivot 565 and the bottom ends of frames 564 are pivotably coupled to one another about a pivot 567 where the pivot axes of pivots 565, 567 are coaxial with one another. Further, frame components 562, 564 define a nested configuration, e.g., wherein one of the frame components 562, 564 is disposed within the other frame component 562, 564, to enable pivoting of frame components 562, 564 to a co-planar orientation wherein structural frame 553 defines a substantially flat configuration (FIGS. 5A and 6A). The substantially flat configuration of structural frame 553 may correspond to the storage condition thereof (FIGS. 5A and 6A) and frame components 562, 564 may be pivoted relative to one another from the storage condition to a use condition (FIGS. 5B and 5B) wherein frame components 562, 564 are substantially perpendicular relative to one another.

Structural frame 553 may also include structure(s) defining eyelets at the top and/or bottom of collection vessel 550 connected thereto either directly or indirectly, e.g., via additional framing or other structure(s). Additionally or alternatively, such structures may be coupled to body 552. Further, body 552 may include one or more ports defined therethrough. In embodiments, bottom eyelets may be omitted and structural frame 553 relied upon to provide the longitudinal structural support to collection vessel 550.

Figure 7B:
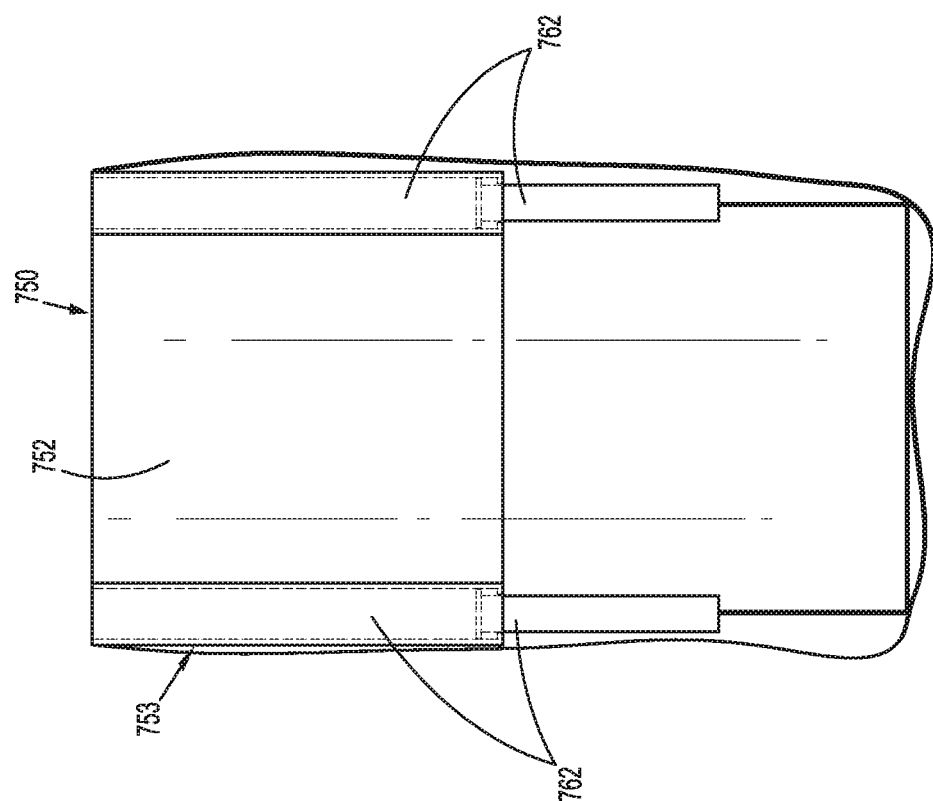
FIG. 7B is a side view of the collection vessel of FIG. 7A, disposed in a use condition.
Figure 7A:
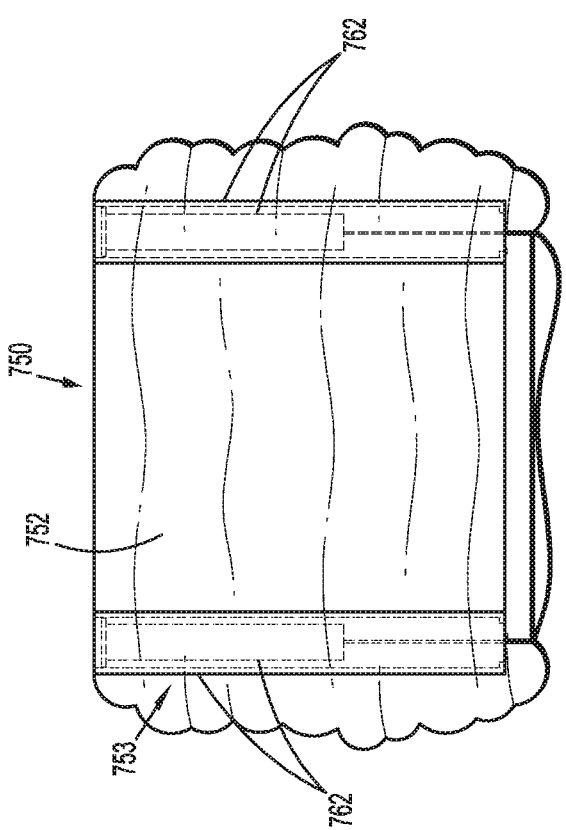
FIG. 7A is a side view of yet another collection vessel configured for use with the collection system of FIG. 2A, disposed in a storage condition.

FIGS. 7A and 7B illustrate another collection vessel provided in accordance with the present disclosure is shown generally identified by reference numeral 750. Collection vessel 750 is similar to and may include any of the features of collection vessels 250 (FIGS. 2A and 2B), 350 (FIG. 3), 450 (FIGS. 4A and 4B), 550 (FIGS. 5A-6B) expect as specifically contradicted below. Further, collection vessel 750 may be configured for use with a collection system e.g., collection system 200 (FIGS. 2A and 2B) or other suitable collection system, and/or a surgical system, e.g., surgical system 100 (FIG. 1) or any other suitable surgical system.

Collection vessel 750 includes a body 752. Body 752 may include closed top and bottom ends or collection vessel 750 may include top and/or bottom plates sealing the top and/or bottom ends, respectively, of body 752. Collection vessel 750 further includes a structural frame 753 including one or more sets of telescoping frame components 762. As illustrated in FIGS. 7A and 7B, two diametrically opposed sets of telescopic frame components 762 are provided; however, greater or fewer sets are also contemplated. The telescopic frame components 762 may define any suitable configuration extending about any portion or the entirety of the circumference of body 752, e.g., post-shaped, ring-shaped, arc-shaped, etc.

At least the outer-most telescoping frame component 762 of each set is connected to a portion of body 752. In embodiments, the outer-most and inner-most telescoping frame components 762 are connected towards the top and bottom, respectively, of body 752 such that, as telescoping frame component 762 are extended apart from one another, body 752 is extended and such that as telescoping frame components 762 are collapsed towards one another, body 752 is collapsed. In embodiments, each of the telescoping frame component 762 of each set is connected to the body 752 such that the telescoping frame components 762 are attached along the length of body 752.

The collapsed positions of telescoping frame components 762 and body 752 correspond to the storage condition of collection vessel 750 (FIG. 7A) while the extended positions of telescoping frame components 762 and body 752 correspond to the use condition of collection vessel 750 (FIG. 7B). Telescoping frame components 762 may be extended to thereby extend body 752 prior to use, or may be extended along with body 752 under gravity as a result the weight of the fluid, tissue, and/or debris filling body 752 during use. In embodiments where telescoping frame components 762 are extended under gravity, telescoping frame components 762 may be extended consecutively or simultaneously and/or may be extended continuously or incrementally.

In embodiments where top and/or bottom plates are provided, either or both may include eyelets to facilitate attachment thereof to a mounting stand, e.g., mounting stand 210 (FIGS. 2A and 2B). Alternatively or additionally, bottom eyelets may be omitted with extended telescoping frame components 762 (which may be locked in the extended position) providing longitudinal structural support to body 752. In embodiments where the bottom of collection vessel 750 is not configured to be supported (and wherein telescoping frame components 762 are not locked or otherwise biased towards an extended position), a scale may be incorporated into the bottom plate or otherwise at the bottom of body 752 to weigh fluid, tissue, and/or debris filling body 752 during use. The scale may be configured to provide a suitable output, e.g., an audible tone, when a weight threshold is met or being approached, thereby indicating that collection vessel 750 is full or approaching a full condition.

Figure 8B:
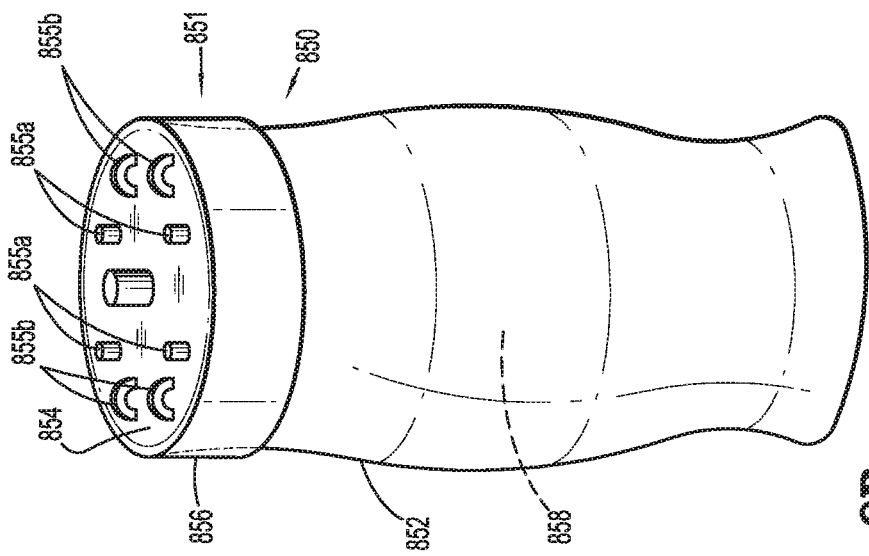
FIG. 8B is a perspective view of the collection vessel of FIG. 8A, disposed in a use condition.
Figure 8A:
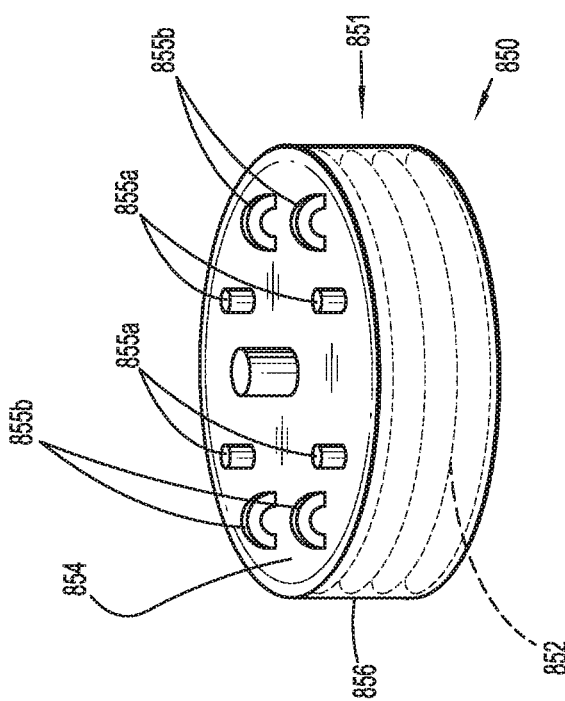
FIG. 8A is a perspective view of still yet another collection vessel configured for use with the collection system of FIG. 2A, disposed in a storage condition.

Shown in FIGS. 8A and 8B is another collection vessel provided in accordance with the present disclosure is shown generally identified by reference numeral 850. Collection vessel 850 is similar to and may include any of the features of collection vessels 250 (FIGS. 2A and 2B), 350 (FIG. 3), 450 (FIGS. 4A and 4B), 550 (FIGS. 5A-6B), 750 (FIGS. 7A and 7B) expect as specifically contradicted below. Further, collection vessel 850 may be configured for use with a collection system e.g., collection system 200 (FIGS. 2A and 2B) or other suitable collection system, and/or a surgical system, e.g., surgical system 100 (FIG. 1) or any other suitable surgical system.

Collection vessel 850 includes a body 852. Body 852 includes an open top end and a closed bottom end. Collection vessel 850 further includes a cassette 851 including a top plate 854 and an outer housing 860. The open top end of body 852 is sealed with top plate 854 to seal interior volume 858 of body 852. Top plate 854 includes a plurality of ports 855*a* and a plurality of eyelets 855*b*, similarly as detailed above. Top plate 854 and cassette 851 may be integrally formed, rigidly attached, or otherwise coupled to one another. As an alternative to body 852 having a closed bottom end, collection vessel 850 may include a bottom plate, similarly as detailed above.

Cassette 851 initially retains body 852 therein in the storage condition of collection vessel 850 (FIG. 8A). Cassette 851 is configured to retain body 852 therein in the absence of fluid, tissue, and/or debris filling interior volume 858 of body 852. As fluid, tissue, and/or debris are suctioned into interior volume 858 of body 852 during use, the weight of the fluid, tissue, and/or debris urges body 852 to depend from cassette 851 under gravity. Body 852 may be configured to unroll, unfurl, unfold, or otherwise depend from cassette 851 upon filling with fluid, tissue, and/or debris and may do so continuously or incrementally.

Figure 9:
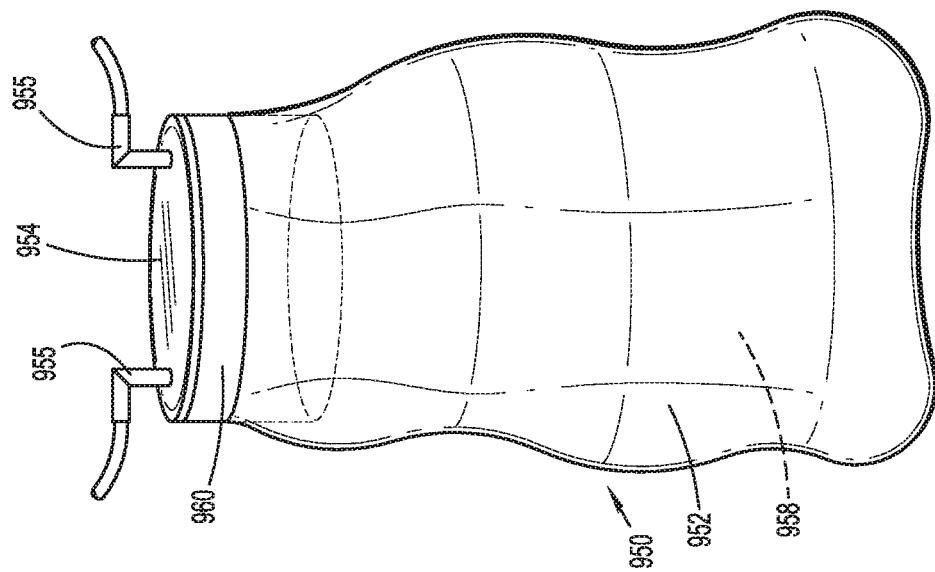
FIG. 9 is a perspective view of another collection system provided in accordance with the present disclosure and configured for use with the surgical system of FIG. 1.

Referring to FIG. 9, another collection vessel provided in accordance with the present disclosure is shown generally identified by reference numeral 950. Collection vessel 950 is similar to and may include any of the features of collection vessels 250 (FIGS. 2A and 2B), 350 (FIG. 3), 450 (FIGS. 4A and 4B), 550 (FIGS. 5A-6B), 750 (FIGS. 7A and 7B), 850 (FIGS. 8A and 8B) expect as specifically contradicted below. Further, collection vessel 950 may be configured for use with a collection system e.g., collection system 200 (FIGS. 2A and 2B) or other suitable collection system, and/or a surgical system, e.g., surgical system 100 (FIG. 1) or any other suitable surgical system.

Collection vessel 950 includes a body 952, a top plate 954, and a support cylinder 960. Body 952 includes an open top end and a closed bottom end. The open top end of body 952 is sealed with top plate 954 to seal interior volume 958 of body 952. Top plate 954 includes a plurality of ports 955 and may include a plurality of eyelets, similarly as detailed above. Top plate 954 and support cylinder 960 may be integrally formed, rigidly attached, or otherwise coupled to one another. As an alternative to body 952 having a closed bottom end, collection vessel 950 may include a bottom plate, similarly as detailed above.

Support cylinder 960 extends from top plate 954 towards the bottom end of body 952 and is formed from a rigid material. Support cylinder 960 extends only a relatively small portion of the full length of body 952 such that support cylinder 960 defines a relatively small footprint. In embodiments, support cylinder 960 may extend from the top end of body between 10% and 50% of the full length of body 952. Body 952, being flexible, may be furled, tucked, folded, rolled, or otherwise manipulated for positioning substantially within support cylinder 960 in a storage condition and may be unfurled, untucked, unfolded, unrolled, or otherwise manipulated for extension from support cylinder 960 to a use position prior to use. Alternatively, body 952 may be extended upon filling with fluid, tissue, and/or debris and may do so continuously or incrementally.

Figure 10A:
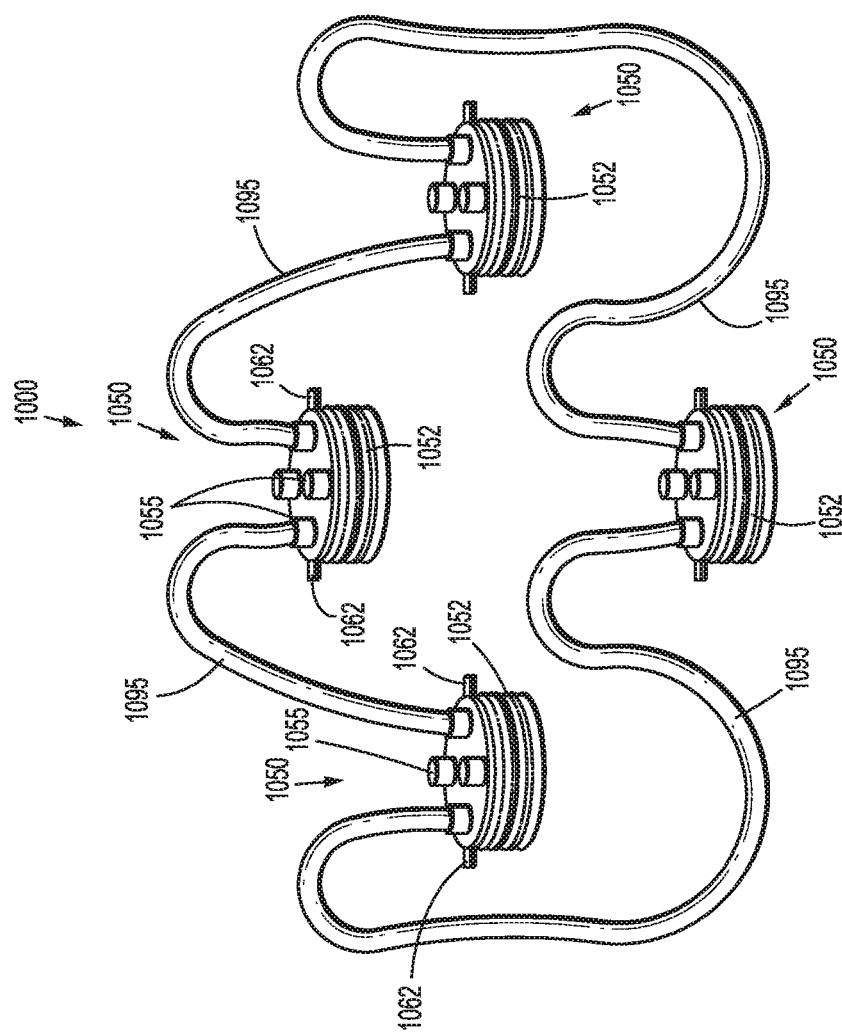
FIG. 10A is a perspective view of another collection system provided in accordance with the present disclosure and configured for use with the surgical system of FIG. 1, including collection vessels connected via connection tubing, disposed in a storage condition.
Figure 10B:
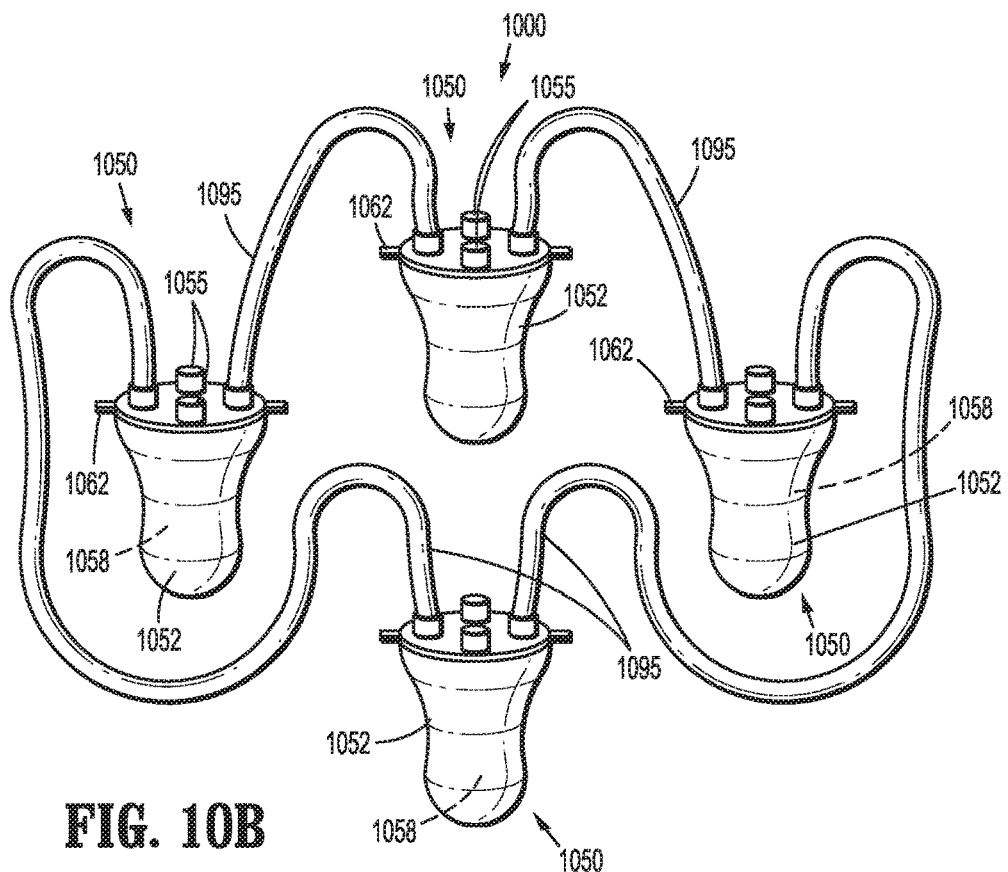
FIG. 10B is a perspective view of the collection vessels of the collection system of FIG. 10A disposed in a use condition.
Figure 10C:
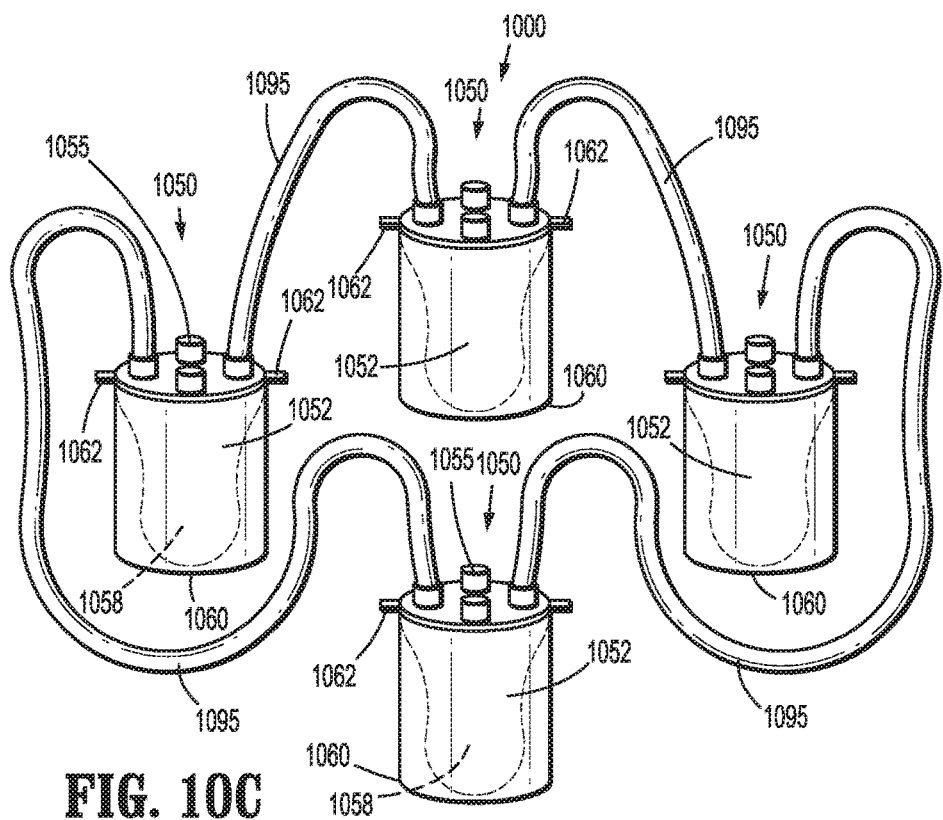
FIG. 10C is a perspective view of the collection vessels of the collection system of FIG. 10A disposed in the use condition and engaged within containers of the collection system of FIG. 10A.

With reference to FIGS. 10A-10C, another collection system provided in accordance with the present disclosure is shown generally identified by reference numeral 1000. Collection system 1000 includes a plurality of collection vessels 1050, connection tubing 1095, and a plurality of retention canisters 1060. Collection system 1000 may include any of the features of collection system 200 (FIGS. 2A and 2B) except as explicitly contradicted below.

Each collection vessel 1050 includes a body 1052 defining a closed bottom end and an open top end and a top plate 1054 sealed to the open top end of body 1052 about the annular perimeter of the body 1052 to seal the interior volume 1058 of the collection vessel 1050. Each top plate 1054 defines a disc-shaped configuration and may be formed from a rigid or semi-rigid material. Alternatively, each top plate 1054 may be formed at least particularly from a flexible material with rigid support portions, e.g., a rigid outer annular support ring. Each top plate 1054 includes a plurality of ports 1055 defined therethrough. Two of the ports 1055 of each top plate 1054 include connection tubing 1095 permanently coupled thereto (although releasable coupling is also contemplated). Connection tubing 1095 interconnects the top plate 1054 of each collection vessel 1050 with the top plate 1054 of each of the adjacent collection vessels 1050. Permanently coupling the collection vessels 1050 in this manner reduces assembly and preparation time at the end user. One or more additional ports 1055 are provided on the top plates 1054 of at least two of the collection vessels 1050, for connection of outflow tubing 180 (FIG. 1) and vacuum tubing 190 (FIG. 1) to the plurality of collection vessels 1050. Outflow tubing 180 (FIG. 1) and vacuum tubing 190 (FIG. 1) may likewise be permanently coupled to these ports 1055 or may be releasably coupled thereto.

Each top plate 1054 further includes a plurality of engagement fingers 1062 extending radially outwardly therefrom, e.g., a pair of diametrically opposed engagement fingers 1062. Each collection vessel 1050 is configured for positioning within a corresponding retention canister 1060 with engagement fingers 1062 snapping into engagement, sitting atop, or otherwise engaging the open upper rim of the corresponding retention canister 1060 such that top plates 1054 are supported extending across the open upper rim of the corresponding retention canister 1060 while bodies 1052 depend from top plates 1054 into the corresponding retention canisters 1060. Retention canisters 1060 are rigid, reusable structures and are generally inhibited from contact with the fluids, tissue, and debris suctioned into bodies 1052 of collection vessels 1050 with bodies 1052 acting as liners for canisters 1060. Of course, retention canisters 1060 are still required to be sterilized or otherwise cleaned before reuse.

The above-detailed collection canisters 1050 are readily collapsible to and/or initially provided in a collapsed configuration corresponding to a storage condition of collection vessels 1050 (FIG. 10A). In preparation for use, bodies 1052 of collection vessels 1050 are unfurled, untucked, unfolded, unrolled, or otherwise extended to achieve a use condition of collection vessels 1050 (FIG. 10B) prior to use. Next, to complete set-up, each collection vessels 1050 is loaded into and engaged with a corresponding retention canister 1060 and outflow tubing 180 (FIG. 1) and vacuum tubing 190 (FIG. 1) are connected. As an alternatively to bodies 1052 being extended prior to use, collection vessels 1050 may be loaded into and engaged with retention canisters 1060 in the storage condition and may be extended upon filling with fluid, tissue, and/or debris during use.

Turning to FIG. 11, another collection system provided in accordance with the present disclosure is shown generally identified by reference numeral 1100. Collection system 1100 includes a plurality of collection vessels 1150, connection tubing 1195, and a plurality of retention canisters 1160. Collection system 1100 may include any of the features of collection systems 200 (FIGS. 2A and 2B), 1000 (FIGS. 10A-10C) except as explicitly contradicted below.

Each collection vessel 1150 includes a body 1152 defining a closed bottom end and an open top end and a top plate 1154 sealed to the open top end of body 1152 about the annular perimeter of the body 1152 to seal the interior volume 1158 of the collection vessel 1150. Each top plate 1154 defines a disc-shaped configuration and may be formed from a rigid or semi-rigid material. Alternatively, each top plate 1154 may be formed at least particularly from a flexible material with rigid support portions. Each top plate 1154 includes a plurality of ports 1155 defined therethrough.

Two of the ports 1155 of each top plate 1154 include connection tubing 1195 permanently coupled thereto (although releasable coupling is also contemplated). Connection tubing 1195 interconnects the top plate 1154 of each collection vessel 1150 with the top plate 1154 of each of the adjacent collection vessels 1150. Permanently coupling the collection vessels 1150 in this manner reduces assembly and preparation time at the end user. One or more additional ports 1155 are provided on the top plate 1154 of at least one of the collection vessels 1150, for connection of outflow tubing 180 (FIG. 1) to the plurality of collection vessels 1150. Outflow tubing 180 (FIG. 1) may likewise be permanently coupled to the port(s) 1155 or may be releasably coupled thereto.

Each top plate 1154 further includes an outer sealing member 1162, e.g., a gasket, disposed about the outer periphery thereof. Each collection vessel 1150 is configured for positioning within a corresponding retention canister 1160 with sealing member 1162 establishing a fluid tight seal about the interior surface of the corresponding retention canister 1160, e.g., towards the open end thereof. In this manner, the interior volume 1164 of each retention canister 1160 is sealed closed.

Each retention canister 1160 further includes a vacuum line 1166 coupled to the interior volume 1164 thereof, e.g., via a port defined through the side wall of the retention canister 1162. Each vacuum line 1166, in turn, is coupled to a vacuum source "V," e.g., vacuum pump 139 of control console 130 (see FIG. 1) or a separate vacuum source. The vacuum source "V" applies suction to create vacuum within the interior volume 1164 of each retention canister 1160. By virtue of the bodies 1152 of collection vessels 1150 being formed from a flexible material, disposed within interior volumes 1164 of corresponding retention canisters 1160, and sealed therein via sealing members 1162, the application of vacuum within interior volumes 1164 provides suction within interior volume 1158 of bodies 1152 of collection vessels 1150 and outflow tubing 180 (FIG. 1) to thereby suction fluid, tissue, and debris through surgical instrument 110 (FIG. 1), outflow tubing 180 (FIG. 1) and into interior volumes 1158.

The above-detailed collection vessels 1150 are readily collapsible to and/or initially provided in a collapsed configuration corresponding to a storage condition of collection vessels 1150. In preparation for use, bodies 1152 of collection vessels 1150 are unfurled, untucked, unfolded, unrolled, or otherwise extended to achieve a use condition of collection vessels 1150 prior to use. Next, to complete set-up, each collection vessels 1150 is loaded into and engaged with a corresponding retention canister 1160 and outflow tubing 180 (FIG. 1) is connected. As such, set-up is facilitated. Further, retention canisters 1160 are rigid, reusable structures and are generally inhibited from contact with the fluids, tissue, and debris suctioned into bodies 1152 of collection vessels 1150 with bodies 1152 acting as liners for vessels 1160. Of course, retention canisters 1160 are still required to be sterilized or otherwise cleaned before reuse.

Referring to FIGS. 12A and 12B, outflow tubing configured for use with any of the above-detailed collection systems and/or collection vessels is shown generally identified by reference numeral 1280. Outflow tubing 1280 may further be configured for use with a surgical system, e.g., surgical system 100 (FIG. 1) or any other suitable surgical system.

As detailed above, the outflow tubing is configured to enable fluid, tissue, and debris to be suctioned through the surgical instrument, e.g., surgical instrument 110 (FIG. 1), during use and deposited in a collection vessel 1250. In embodiments, in addition to outflow fluid, tissue, and debris suctioned through the surgical instrument, other components may receive and/or collect outflow fluid, tissue, and/or debris that needs to be deposited in a collection vessel.

In order accommodate the outflow from multiple components, outflow tubing 1280 includes a plurality of branches, e.g., a first outflow branch 1282, a second outflow branch 1284, and a third outflow branch 1286. First outflow branch 1282 may, for example, connect to a tissue resecting surgical instrument, e.g., surgical instrument 110 (FIG. 1), to receive outflow therefrom; second outflow branch 1284 may, for example, connect to an insertion device (not shown) configured to receive the tissue resecting surgical instrument therethrough, e.g., an endoscope (hysteroscope), sheath, etc., to receive outflow therefrom; and third outflow branch 1286 may, for example, connect to a surgical accessory, e.g., a surgical drape, to receive outflow therefrom.

Outflow tubing 1280 further includes a base portion 1288 to which branches 1282, 1284, 1286 are joined. Base portion 1288 of outflow tubing 1280 is configured to couple to a port 1255 of collection vessel 1250. Collection vessel 1250 is further configured to connect to a vacuum source, e.g., vacuum pump 139 of control console 130 (FIG. 1), via vacuum tubing 1290 to apply vacuum within internal volume 1258 of collection vessel 1250, thereby providing suction through base portion 1288 and each of the plurality of branches 1282, 1284, 1286 of outflow tubing 1280. However, since the different instruments, accessories, and/or components may require different amounts of suction to facilitate drawing tissue therefrom through outflow tubing 1280 into collection vessel 1250, a flow restrictor 1285, 1287 is disposed within one or more of the plurality of branches 1282, 1284, 1286. For example, a first flow restrictor 1285 may be disposed within second branch 1284, and a second flow restrictor 1287 may be disposed within third branch 1286. First branch 1282 may not include a flow restriction (as shown) although, in embodiments, any or all of the plurality of branches 1282, 1284, 1286 may include flow restrictors. Each of the flow restrictors 1285, 1287 may be a fixed flow limiter, a variable valve, or other suitable flow restrictor. The flow restrictors 1285, 1287 may be removable from branches 1284, 1286, respectively, to enable an appropriate flow restrictor 1285, 1287 to be installed depending upon the instrument, accessory, or component coupled to that branch 1284, 1286. Further, flow restrictors 1285, 1287 may be configured, in at least one variable setting thereof, to fully occlude fluid flow through branches 1284, 1286, respectively, such as, for example, when no instrument, accessory, or other component is coupled to that respective branch 1284, 1286.

The above-detailed configuration of outflow tubing 1280 enables a single tubing 1280 to collect fluid, tissue, and debris from multiple instruments, accessories, and/or components with variable suction pressure for depositing such fluid, tissue, and debris in collection vessel 1250.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A collection system for collecting outflow from a hysteroscopic surgical procedure, the collection system comprising:

a collection vessel defining an internal volume and including a top portion and a bottom portion, the collection vessel including a top plate at the top portion of the collection vessel and a body extending from the top plate, the collection vessel transitionable between a collapsed configuration and an expanded configuration;

a mounting stand including an upper retainer and a lower retainer, the upper retainer of the mounting stand including at least one support arm configured to retain the top portion of the collection vessel and the lower retainer of the mounting stand including at least one other support arm configured to retain the bottom portion of the collection vessel, the at least one support arm and the at least one other support arm of the upper and lower retainers, respectively, configured to retain the collection vessel thereon in the expanded configuration;

at least one top eyelet extending from a face of the top plate opposite the body, the at least one top eyelet configured to receive the at least one support arm of the upper retainer therein to support the top portion of the collection vessel;

at least one bottom eyelet extending substantially vertically from the bottom portion of the collection vessel, the at least one bottom eyelet configured to receive the at least one other support arm of the lower retainer therein to support the bottom portion of the collection vessel; and a support frame arranged in the collection vessel, the support frame defining a helical shape extending between the top portion and the bottom portion of the collection vessel, the support frame configured to provide structural support to the collection vessel.

2. The collection system according to claim 1, wherein the collection vessel includes a bottom plate coupled to the body at the bottom portion of the collection vessel, the at least one bottom eyelet extending substantially vertically from the bottom plate of the collection vessel.

3. The collection system according to claim 1, wherein the top plate includes at least one port configured to connect to tubing such that the tubing is disposed in communication with the internal volume.

4. The collection system according to claim 1, wherein the upper retainer includes at least one upper support arm configured to retain the top portion of the collection vessel thereon and wherein the lower retainer includes at least one lower support arm configured to retain the bottom portion of the collection vessel thereon.

5. The collection system according to claim 1, wherein the mounting stand includes at least one vertical support and wherein the at least one other support arm extends from the at least one vertical support.

6. The collection system according to claim 5, wherein the at least one other support arm extends substantially horizontally with respect to the at least one vertical support.

7. The collection system according to claim 1, wherein the support frame includes at least one wire.

8. The collection system according to claim 1, wherein the support frame is arranged between two layers of the body of the collection vessel.

9. The collection system according to claim 1, wherein the support frame is configured to provide longitudinal support to the collection vessel when it is transitioned between a storage condition and a use condition.

10. A surgical system, comprising:
a surgical instrument;
a vacuum pump; and
a collection system for collecting outflow from the surgical instrument, the collection system comprising:

a collection vessel defining an internal volume and including a top portion and a bottom portion, the collection vessel including a top plate at the top portion of the collection vessel and a body extending from the top plate, the collection vessel transitionable between a collapsed configuration and an expanded configuration;

a mounting stand including an upper retainer and a lower retainer, the upper retainer of the mounting stand configured to retain the top portion of the collection vessel and the lower retainer of the mounting stand configured to retain the bottom portion of the collection vessel, the upper and lower retainers configured to retain the collection vessel thereon in the expanded configuration;

at least one top eyelet extending from a face of the top plate opposite the body, the at least one top eyelet configured to receive at least one support arm therein to support the top portion of the collection vessel;

outflow tubing connecting the surgical instrument with the internal volume of the collection vessel;

vacuum tubing connecting the vacuum pump with the internal volume of the collection vessel;

at least one bottom eyelet extending substantially vertically from the bottom portion of the collection vessel, the at least one bottom eyelet configured to receive at least one other support arm therein to support the bottom portion of the collection vessel; and a support frame arranged in the collection vessel, the support frame defining a helical shape extending between the top portion and the bottom portion of the collection vessel, the support frame configured to provide structural support to the collection vessel.

11. The surgical system according to claim 10, wherein the top plate includes first and second ports to connect the outflow tubing and the vacuum tubing to the internal volume of the collection vessel.

12. The surgical system according to claim 10, wherein the support frame is configured to at least one of telescope, pivot, flex, or tilt to transition the collection vessel between the collapsed configuration and the expanded configuration.

13. The surgical system according to claim 10, wherein the surgical instrument is a tissue resection instrument configured to receive outflow from a surgical site.

14. The surgical system according to claim 13, further comprising a control console configured to control the tissue resection instrument and including the vacuum pump disposed therein.

15. The surgical system according to claim 10, wherein the mounting stand includes at least one vertical support and wherein the at least one other support arm extends from the at least one vertical support.

16. The surgical system according to claim 15, wherein the at least one other support arm extends substantially horizontally with respect to the at least one vertical support.

17. The collection system according to claim 10, wherein the support frame includes at least one wire.

18. The collection system according to claim 10, wherein the support frame is arranged between two layers of the body of the collection vessel.

19. The collection system according to claim 10, wherein the support frame is configured to provide longitudinal support to the collection vessel when it is transitioned between a storage condition and a use condition.

* * * * *